US008844366B2

(12) United States Patent
Warren et al.

(10) Patent No.: US 8,844,366 B2
(45) Date of Patent: Sep. 30, 2014

(54) THREE DIMENSIONAL TRANSDUCER

(75) Inventors: Oden Lee Warren, New Brighton, MN (US); Syed Amanulla Syed Asif, Bloomington, MN (US); Yunje Oh, Medina, MN (US); Yuxin Feng, Plymouth, MN (US); Edward Cyrankowski, Woodbury, MN (US); Ryan Major, Crystal, MN (US)

(73) Assignee: Hysitron, Inc., Eden Prairie, MN (US)

( * ) Notice: Subject to any disclaimer, the term of this patent is extended or adjusted under 35 U.S.C. 154(b) by 0 days.

(21) Appl. No.: 14/004,138

(22) PCT Filed: Mar. 9, 2012

(86) PCT No.: PCT/US2012/028601
§ 371 (c)(1),
(2), (4) Date: Oct. 30, 2013

(87) PCT Pub. No.: WO2012/122523
PCT Pub. Date: Sep. 13, 2012

(65) Prior Publication Data
US 2014/0150562 A1 Jun. 5, 2014

Related U.S. Application Data

(60) Provisional application No. 61/451,058, filed on Mar. 9, 2011.

(51) Int. Cl.
*G01B 7/16* (2006.01)
(52) U.S. Cl.
CPC ........................................ *G01B 7/16* (2013.01)
USPC .............................................................. 73/780
(58) Field of Classification Search
USPC .............................. 73/780, 862.337, 862, 626
See application file for complete search history.

(56) References Cited

U.S. PATENT DOCUMENTS 4,716,656 A * 1/1988 Maddock et al. ................ 33/503
4,924,173 A * 5/1990 Dishman ........................ 324/690
(Continued)

FOREIGN PATENT DOCUMENTS

WO WO-2012122523 A1 9/2012

OTHER PUBLICATIONS

"International Application Serial No. PCT/US2012/028601, International Preliminary Report on Patentability mailed Apr. 1, 2013", 50 pgs.

(Continued)

*Primary Examiner* — Max Noori
(74) *Attorney, Agent, or Firm* — Schwegman Lundberg & Woessner, P.A.

(57) ABSTRACT

A testing instrument for mechanical testing at nano or micron scale includes a transducer body, and a coupling shaft coupled with a probe tip. A transducer body houses a capacitor. The capacitor includes first and second counter electrodes and a center electrode assembly interposed therebetween. The center electrode assembly is movable with the coupling shaft relative to the first and second counter electrodes, for instance in one or more of dimensions including laterally and normally. The center electrode assembly includes a center plate coupled with the coupling shaft and one or more springs extending from the center plate. Upper and lower plates are coupled with the center plate and cover the center plate and the one or more springs. A shaft support assembly includes one or more support elements coupled along the coupling shaft. The shaft support assembly provides lateral support to the coupling shaft.

20 Claims, 18 Drawing Sheets

(56) References Cited

U.S. PATENT DOCUMENTS

| | | | |
|---|---|---|---|
| 4,960,132 A * | 10/1990 | Habekost | 600/589 |
| 5,006,952 A | 4/1991 | Thomas | |
| 5,224,383 A * | 7/1993 | Pinto et al. | 73/706 |
| 6,552,523 B2 * | 4/2003 | Huard | 324/72.5 |
| 6,579,149 B2 * | 6/2003 | Lebel et al. | 451/6 |
| 6,820,493 B1 | 11/2004 | Bonin | |
| 7,414,413 B2 * | 8/2008 | Crum et al. | 324/662 |
| 7,574,899 B2 * | 8/2009 | Minott et al. | 73/61.43 |
| 7,654,159 B2 * | 2/2010 | Enoksson et al. | 73/862.68 |
| 7,798,011 B2 | 9/2010 | Warren et al. | |
| 2007/0276292 A1 * | 11/2007 | Hansma et al. | 600/587 |
| 2010/0132441 A1 | 6/2010 | Oh et al. | |
| 2010/0160356 A1 | 6/2010 | Heinrich et al. | |
| 2014/0069199 A1 * | 3/2014 | Barron et al. | 73/724 |
| 2014/0083163 A1 * | 3/2014 | Merklein et al. | 73/1.79 |

OTHER PUBLICATIONS

"International Application Serial No. PCT/US2012/028601, International Search Report mailed Jul. 6, 2012", 4 pgs.
"International Application Serial No. PCT/US2012/028601, Written Opinion mailed Jul. 6, 2012", 21 pgs.

* cited by examiner

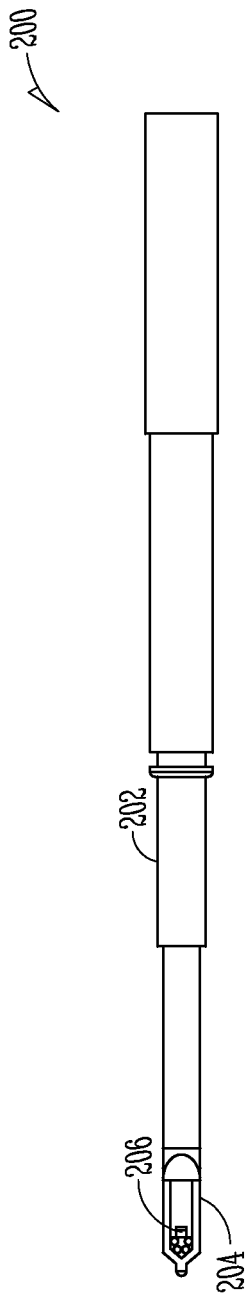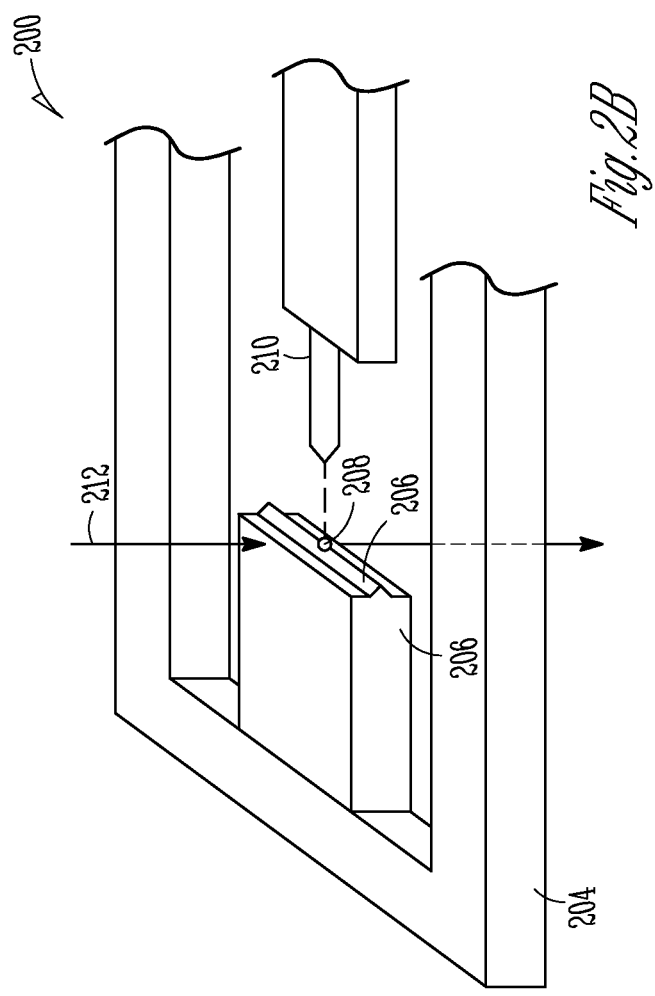

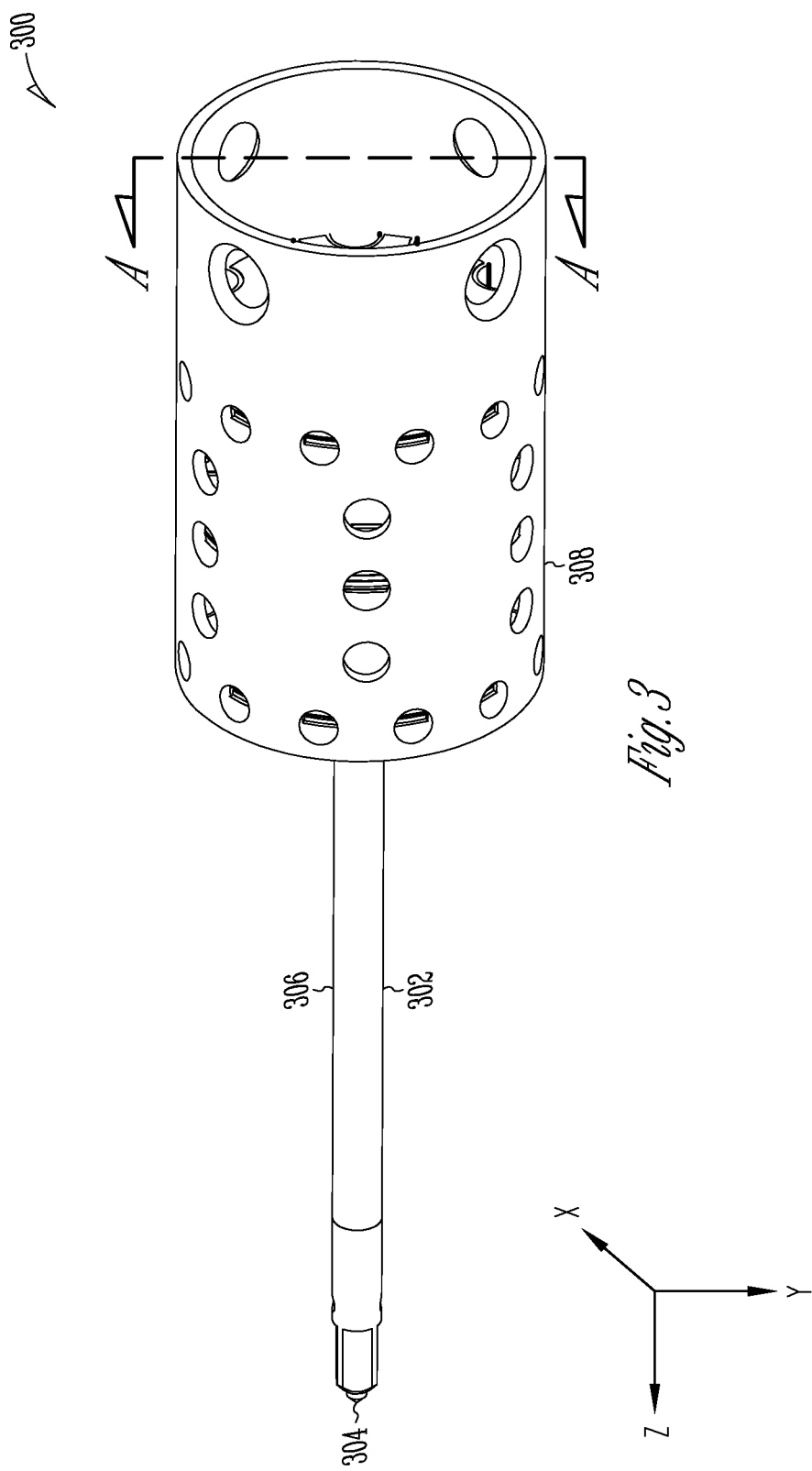

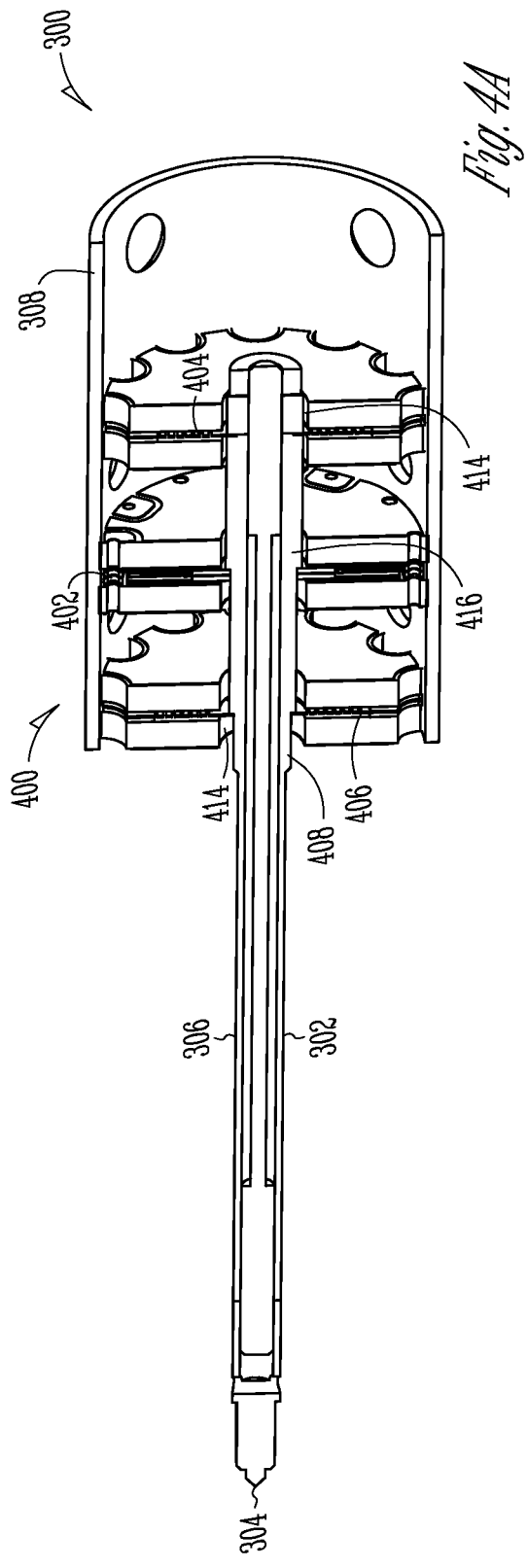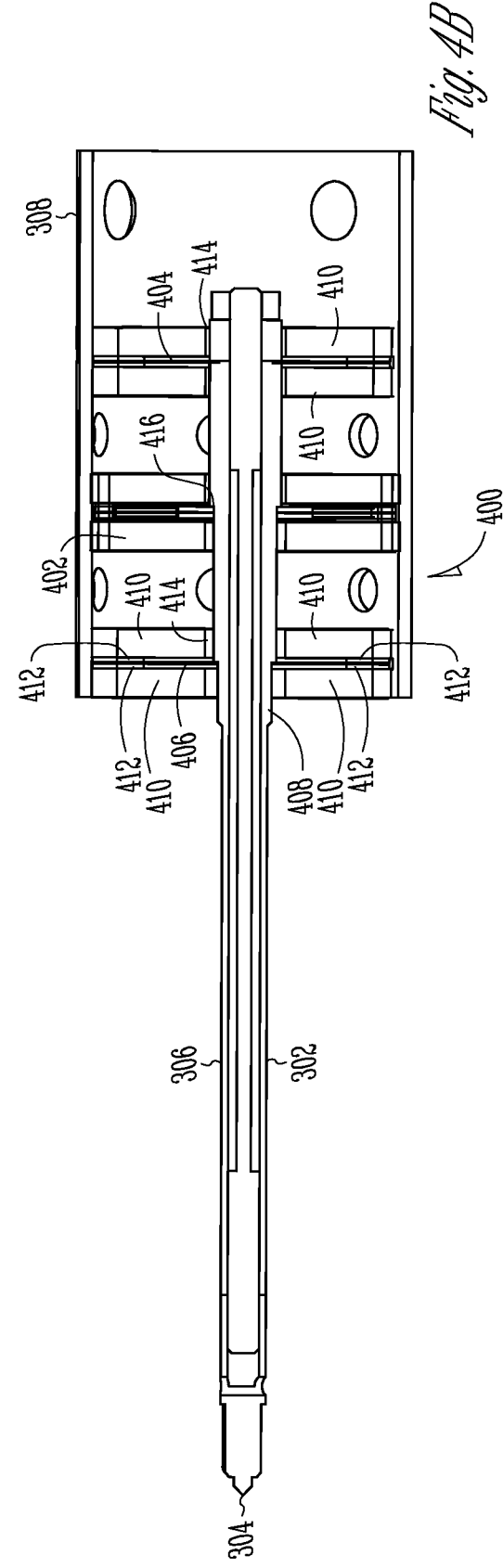

1700

1702
ENGAGING A PROBE TIP WITH A SUBJECT, THE PROBE TIP IS COUPLED WITH A COUPLING SHAFT AND THE COUPLING SHAFT IS COUPLED WITH A CAPACITOR ASSEMBLY, WHEREIN THE CAPACITOR ASSEMBLY INCLUDES:
- A CENTER ELECTRODE ASSEMBLY MOVABLE WITH THE COUPLING SHAFT, THE CENTER ELECTRODE ASSEMBLY INCLUDES UPPER AND LOWER PLATES COVERING A CENTER PLATE AND ONE OR MORE SPRINGS EXTENDING FROM THE CENTER PLATE, AND
- FIRST AND SECOND COUNTER ELECTRODES FACING THE UPPER AND LOWER PLATES, EACH OF THE FIRST AND SECOND COUNTER ELECTRODES INCLUDES A PLURALITY OF SECTIONS, AND EACH OF THE SECTIONS IS ELECTRICALLY ISOLATED FROM THE OTHER SECTIONS

1704
TRANSMITTING A PLURALITY OF EXCITATION SIGNALS TO THE PLURALITY OF SECTIONS, EACH OF THE EXCITATION SIGNALS ASSOCIATED WITH EACH SECTION IS DIFFERENT FROM THE EXCITATION SIGNALS TRANSMITTED TO THE OTHER SECTIONS

1706
MEASURING ONE OR MORE OF THE DISPLACEMENT OF THE PROBE TIP AND THE FORCE INCIDENT ON THE PROBE TIP ACCORDING TO MEASURABLE ELECTRICAL CHARACTERISTICS IN A COMPOSITE OUTPUT SIGNAL RECEIVED FROM THE CENTER ELECTRODE ASSEMBLY BASED ON THE PLURALITY OF EXCITATION SIGNALS

*Fig. 17*

THREE DIMENSIONAL TRANSDUCER

CLAIM OF PRIORITY

This patent application claims the benefit of priority to International Patent Application Serial No. PCT/US2012/026899, filed on Feb. 28, 2012 and published on Sep. 13, 2012 as WO 2012/121928A1, which claims the benefit of priority to U.S. Provisional Patent Application Ser. No. 61/451,058, entitled THREE DIMENSIONAL TRANSDUCER," filed on Mar. 9, 2011, which is hereby incorporated by reference herein in its entirety.

STATEMENT REGARDING FEDERALLY SPONSORED RESEARCH OR DEVELOPMENT

This invention was made with government support under award number DE-FG02-07ER84812 awarded by the United States Department of Energy. The government has certain rights in this invention.

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever. The following notice applies to the software and data as described below and in the drawings that form a part of this document: Copyright Hysitron, Inc., All Rights Reserved.

TECHNICAL FIELD

Nano and micron scale testing and transducers for the same.

BACKGROUND

Tribology mechanical testing includes the investigation of mechanical properties of materials. At the submicron scale (e.g., nano scale), subjects are viewed with a variety of microscopes including transmission electron microscopes (TEM), scanning electron microscopes (SEM) and the like. The subjects are tested mechanically to observe and determine the mechanical properties of the subjects. In some examples, mechanical testing includes moving a probe in one or more of lateral and normal directions relative to the subject. For instance, a probe indents the subject or laterally scratches across the subject and an attached transducer determines one or more of a variety of mechanical properties including elastic modulus and hardness of the subject material.

The probes used are oriented, in at least some designs, horizontally relative to gravity and a vertical electron source. Further, the probes extend horizontally from an actuator to facilitate engagement with a subject and measurement of the mechanical properties. The length of the probe and its stiffness negatively impact the accuracy of the probe for testing of mechanical properties. In some examples, the transducer attached to the probe experiences large amounts of tip displacement noise proportional to the length of the probe. Additionally, the transducer experiences large tip offset from true horizontal because of gravity. The tip offset is proportional to the stiffness of the probe as well as its length. Tip offset caused by gravity creates an uneven gap between capacitor plates within the transducer and negatively affects the ability of transducer circuitry to accurately measure actual mechanical movement of the probe during testing. For example, the uneven gap between plates saturates a circuit board sensing range thereby providing inaccurate measurements of lateral movement.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 2A is a side view showing one example of a test subject holder including a sample stage and a housing for a mechanical testing instrument.

FIG. 2B is a schematic view of a test subject holder with a sample stage and a mechanical testing instrument.

FIG. 3 is a perspective view of one example of a mechanical testing instrument including a probe and a transducer body.

FIG. 4A is a cross sectional perspective view of the mechanical testing instrument shown in FIG. 3 taken along line A-A.

FIG. 4B is a cross sectional view of the mechanical testing instrument shown in FIG. 3 taken along line A-A.

FIG. 17 is a block diagram showing a method for sensing changes in electrical characteristics in a mechanical testing instrument.

DETAILED DESCRIPTION

Figure 1:
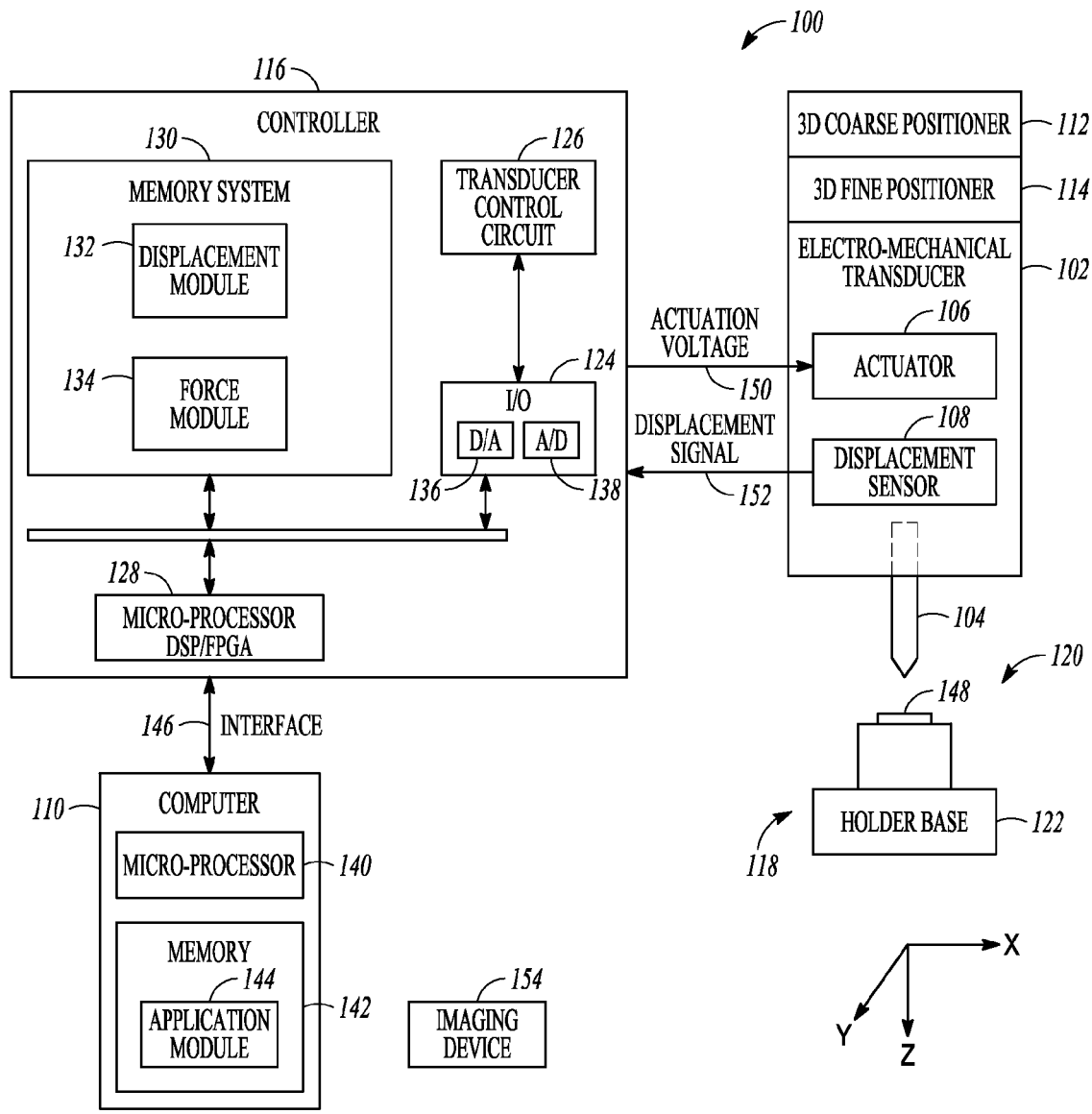
FIG. 1 is a block diagram showing one example of a mechanical test system configured for testing of a sample at a nano or micron scale.

In the following detailed description, reference is made to the accompanying drawings which form a part hereof, and in which is shown by way of illustration how specific embodiments of the present disclosure may be practiced. In this regard, directional terminology, such as "top," "bottom," "front," "back," "leading," "trailing," etc., is used with reference to the orientation of the Figure(s) being described. Because components of embodiments of the present invention can be positioned in a number of different orientations, the directional terminology is used for purposes of illustration and is in no way limiting. These embodiments are described in sufficient detail to enable those skilled in the art to practice aspects of this disclosure, and it is to be understood that other embodiments may be utilized and that structural changes may be made without departing from the scope of the present disclosure. Therefore, the following detailed description is not to be taken in a limiting sense, and the scope of the present disclosure is defined by the appended claims and their equivalents.

According to embodiments described herein, a system and method are provided for mechanically testing small test subjects at the nano and micro scales (i.e., sub-micron scale), including, but not limited to, nanostructures, thin films and the like. Such testing is performed, in one example, to determine the mechanical properties of the materials composing the subjects.

The systems and methods described herein are used for nanoindentation and tribology testing. Nanoindentation and tribology are techniques for probing small volumes of solids for the purpose of quantifying their mechanical properties. These techniques use an instrument referred to as a nanoindenter, tribometer and the like to conduct nanoindentation and tribology testing (i.e., movement of one surface relatively over another surface). The probes used in nanoindentation and tribology testing usually include a tip made of a hard material (e.g. diamond, sapphire and the like). The probe tip is shaped to a well-defined geometry typically having an apical radius of curvature in the range of 10 nm-1 mm. One example of a tip geometry includes a three-sided pyramidal Berkovich geometry.

The systems and methods described herein include a three dimensional transducer for use in nanoindentation and tribology testing. The three dimensional transducer is correspondingly capable of actuation and measurement in lateral (x-y) and normal (z) directions. Further, the systems and methods described herein are configured for used in transmission electron microscopes, scanning electron microscopes and the like. The systems and methods including the three dimensional transducer are further used for, but not limited to, indentation, scratch testing (e.g., wear, scratch resistance, delamination force testing and the like). Further the systems and methods are configured for imaging, for instance imaging of x-y lateral displacement for friction force (or frictional coefficient) mapping and z topography (imaging of peaks and valleys in a sample).

FIG. 1 is a schematic block diagram illustrating an example of a nanomechanical test system 100. The nanomechanical test system 100 (e.g., sub-micron testing on one or multiple micron or nanometer scales) includes a mechanical testing instrument having an electro-mechanical (EM) transducer 102 including a displaceable probe 104, an actuator 106 to displace the probe 104, a displacement sensor 108, a computer 110, a coarse positioner 112, a fine positioner 114, and a controller 116. In one example, the actuator 106 and the displacement sensor 108 are consolidated into a single transducer including, but not limited to, a capacitor.

The nanomechanical test system 100 further includes a test subject holder 118 including a sample stage 120 having a base portion 122 (a holder base). The test subject holder 118 is detachably mounted to the nanomechanical test system 100.

According to one embodiment, the controller 116 includes an input/output module 124, a transducer control circuit 126, a processor 128, such as a microprocessor or digital signal processor (DSP) and/or field programmable gate array (FPGA), and a memory system 130. According to another embodiment, the memory system 130 includes a displacement module 132 and a force module 134. According to another embodiment, the input/output module 124 further includes a D/A converter 136 (DAC), and an A/D converter 138 (ADC).

In one example, the computer 110 includes a processor 140 and a memory system 142 that stores an application module 144. The computer 110 may access and communicate with the controller 116 via an interface 146 (e.g. a USB interface). FIG. 1 shows the computer 110 and controller 116 as separate entities. In other examples, the computer 110 and controller 116 are combined as part of a single processing and control system.

According to one embodiment, the application module 144, displacement module 132, and force module 134 each include instructions respectively stored in memories 130 and 142 and which are accessible and executable by the processor 128. The memories 130 and 142 include, but are not limited to, any number of volatile or non-volatile storage devices such as RAM, flash memory, hard disk drives, CD-ROM drives, DVD drives and the like. In other embodiments, the displacement module 132 and the force module 134 include any combination of hardware and software components configured to perform functions described herein. The software components of the displacement module 132 and the force module 134 are each stored on a medium separate from the processor 128 prior to being stored in the memory system 130, in one example. Examples of such media include a hard disk drive, a flash memory device, a compact disc (e.g. a CD-ROM, CD-R, or CD-RW), and a digital video disc (e.g. a DVD, DVD-R, and DVD-RW), for example.

According to one embodiment, the coarse positioner 112 and the fine positioner 114 enable 3-dimensional positioning (i.e., x-y-z axes in FIG. 1) of the EM transducer 102 and the displaceable probe 104 in the millimeter range with a sub-nanometer resolution. According to one embodiment, final positioning and movement of the displaceable probe 104 is performed by the actuator 106 via the application module 144 on the computer 110 and the controller 116. According to one embodiment, the controller 116 is configured to control and monitor the movement of the displaceable probe 104 and to provide data representative of a displacement of the displaceable probe 104 (from the displacement sensor 108) to the computer 110 through the interface 146. According to one embodiment, the controller 116 is configured to determine and adjust a force applied to a test sample 148 by the displaceable probe 104.

In operation, a user may program the controller 116 with the computer 110 through the application module 144. According to one embodiment, the controller 116, through the force module 134, provides an input or force signal 150 (actuation voltage) to the actuator 106 representative of a desired force for application to the test sample 148 by the displaceable probe 104. In response to the input actuation force signal 150, the actuator 106 drives the displaceable probe 104 toward the sample stage 120 (e.g. along the z-axis in FIG. 1). In another example, the actuator 106 moves the displaceable probe 104 across the sample 148 on the sample stage 120. The displaceable probe 104 contacts and applies the desired force to the test sample 148 (in one or more of lateral or normal directions). The D/A converter 136 converts the input or force signal provided by the force module 134 from digital to analog form which, in turn, is amplified to generate the actuation voltage 150 by the transducer control circuit 126 as provided to the actuator 106.

The displacement sensor 108 comprises a transducer (e.g. a capacitive transducer, and in one example is integral to the actuator 106, also a capacitor) which detects movement of displaceable probe 104 along the x-y-z-axes, and provides a displacement signal 152 to the controller 116 representing measurement of the movement of the displaceable probe 104. In other embodiments, in addition to movement along the z-axis, the displacement sensor 108 detects and provides indication of other types of movement of the displaceable probe 104, such as displacement along one or more of the x or y-axes or rotational movement about one or more of the x or y-axes. The transducer control circuit 126 conditions the displacement signal 152 from the displacement sensor 108 and sends the displacement signal 152 to the A/D converter 138. The A/D converter 138 converts the displacement signal 152 from an analog form, as received from the transducer control circuit 126, to a digital form for processing by the displacement module 132. The displacement module 132, according to one embodiment, communicates measurement of the movement of the displaceable probe 104 to the force module 134 (e.g. for force calculations) and the computer 110 (via interface 146). In another example, the actuation voltage is applied to the actuator 106 to hold the displaceable probe 104 static while another actuator, such as the 3D coarse or fine positioners indents or scratches the sample with the probe 104. The actuator voltage 150 is measured (in a similar manner to the displacement signal 152) and used to determine the force incident on the test sample 148.

According to one embodiment, the controller 116 is further configured to control movement or displacement of displaceable probe 104 in the x- and y-directions relative to sample stage 120, such as by moving the EM transducer 102 relative to the sample stage 120 or by moving the sample stage 102 relative to the EM transducer 102. According to one embodiment, the nanomechanical test system 100 further includes an imaging device 154 comprising an instrument or device such as an electron microscope, an optical microscope, or a scanning probe microscope (SPM) (e.g., an atomic force microscope (AFM)) configured to provide images of the test sample 148 mounted to the sample stage 120, including images of the test sample 148 before, during and after mechanical testing such as indentation, scratch testing, compression, fatigue and fracture testing and the like and video of the same.

Test systems suitable for use with the disclosure include, but are not limited to, optical microscopes, scanning probe microscopes (SPM), electron microscopes (TEM and SEM) and the like.

Referring now to FIG. 2A, one example of a mechanical testing instrument 200, usable for instance with the Nanomechanical Test System 100 shown in FIG. 1, is provided. As shown in FIG. 2A, the mechanical testing instrument 200 includes an outer tube 202 extending toward a test subject holder 204. In one example, the mechanical testing instrument 200 is held within an instrument including, but not limited to, a scanning electron microscope (SEM), a transmission electron microscope (TEM) and the like. The test subject holder 204 at one end of the outer tube 202 includes a sample stage configured for reception of a sample. As will be described in further detail below, the sample is tested with the mechanical testing instrument 200, for instance, while the mechanical testing instrument is positioned within an instrument (e.g., a microscope, such as a TEM and an SEM), and the instrument observes the sample at one or more of, the time prior to mechanical testing, during mechanical testing and after mechanical testing.

Referring now to FIG. 2B, one example of the mechanical testing instrument 200 is shown with the test subject holder 204 positioned adjacent to a probe 210. One example of the probe 210 (also shown schematically in FIG. 1 as feature 104) includes a probe tip and a coupling shaft extending into the mechanical testing instrument 200 where the probe is coupled with a transducer configured to perform one or more of actuation and sensing of displacement and forces incident on the probe through engagement with a sample 208 provided on the sample stage 206. As shown in FIG. 2B, the test subject holder 204 includes the sample stage 206 providing a surface for mounting of the sample 208 for testing with the mechanical testing instrument 200.

An electron beam 212, for instance from a transmission electron microscope, is shown directed through the sample 208. In one example, the mechanical testing instrument 200 is configured to provide in situ mechanical testing of the sample 208 while the sample 208 is mounted on the sample stage 206 within an instrument, such as a microscope (e.g., a transmission electron microscope or scanning electron microscope). In one example, the mechanical testing instrument 200 tests the sample 208 immediately before, during, and after examination of the sample 208 with the electron beam 212 of the microscope. Optionally, the mechanical testing instrument 200 performs a testing procedure on the sample 208 during one or more of the period of time before, during, and after examination of the sample with the electron beam 212 of the microscope.

FIG. 3 shows another example of a mechanical testing instrument 300. In one example, the mechanical testing instrument 300 is positioned within the outer tube 202 shown in FIG. 2A. The mechanical testing instrument 300 shown in FIG. 3 includes a probe 302 extending from a transducer housing 308. The probe 302 in the example provided includes a probe tip 304 coupled with a coupling shaft 306, and the coupling shaft 306 is in turn coupled with a transducer within the transducer housing 308. As previously described above, in one example the probe tip 304 is constructed with a hard and rigid material with known material properties, such as diamond. In another example, the coupling shaft 306 is constructed with materials having a specified lateral stiffness and thereby behaves in a predictable manner when actuated in one or more of the X, Y, and Z axes shown in FIG. 3. In one example, the coupling shaft 306 is constructed with but not limited to alumina.

As will be described in further detail below, the transducer housing 308 includes a transducer configured to displace the probe tip 304 and the coupling shaft 306 in one or more of normal and lateral directions across samples, for instance, a sample such as the sample 208 positioned on the sample stage 206 shown in FIG. 2B. Optionally, the mechanical testing instrument 300 is configured to hold the probe 302, including the probe tip 304, static while the mechanical testing instrument 300 is moved across a sample normally, laterally or a combination of both. Stated another way, the mechanical testing instrument 300 holds the probe tip 304 static while a separate actuator moves the probe tip 304 through an indentation procedure, a scratching procedure, a combination of both, and the like. In such an example, the transducer of the mechanical testing instrument 300 is used to measure forces incident at the probe tip 304 through engagement with the sample but the transducer does not otherwise provide actuation forces. For instance, the mechanical testing instrument 300 does not by itself displace the probe tip 304 relative to the remainder of the mechanical testing instrument. Instead, another actuator, such as a piezo actuator including for example the positioners 112, 114, shown in FIG. 1, coupled to the mechanical testing instrument 300, moves the probe tip 304 (and the remainder of the instrument 300) normally, laterally, a combination of both, and the like relative to a sample such as sample 208 while the tip 304 is otherwise held static relative to the mechanical testing instrument 300.

FIGS. 4A and 4B show cross-sectional views (perspective and side views) of the mechanical testing instrument 300 shown in FIG. 3. As shown in FIGS. 4A and 4B, the mechanical testing instrument 300 includes a transducer assembly 400 having a capacitor assembly 402 and proximal and distal support elements 404, 406 (e.g., support springs) spaced from the capacitor assembly 402 along a shank 408 of the coupling shaft 306. As described in further detail below, the capacitor assembly 402 includes in one example a three plate capacitor configured to actuate the probe tip 304 in three dimensions (e.g., in the x, y and z directions or combinations of one or more of those directions). As previously described above, the capacitor assembly 402 is configured in other examples to hold the coupling shaft 306 and correspondingly hold the probe tip 304 static relative to the remainder of the transducer assembly 400, for instance where the transducer assembly 400 is moved with another actuator, such as a piezo transducer, to indent or laterally move the probe tip 304 relative to a sample. Further, the transducer assembly 400 is configured for measuring displacement of the probe tip 304 and forces incident on the probe tip in three dimensions (e.g., the x, y and z directions). Stated another way, the transducer assembly 400 is a three dimensional (3D) transducer assembly configured for actuation and force and displacement measurements in three dimensions.

As shown, for instance, in FIGS. 4A and 4B, the shank 408 of the coupling shaft 306 is sized and shaped for reception within the capacitor assembly 402 and the proximal and distal support elements 404, 406. The shank 408 is engaged within the capacitor assembly 402 by a single plate of the capacitor as described below. Similarly, the proximal and distal support elements 404, 406 are coupled between the transducer housing 308 and the shank 408. The coupling shaft 306, through the shank 408, is thereby supported at three locations, by the proximal and distal support elements 404, 406 and the capacitor assembly 402. By movably supporting the shank 408 at a plurality of locations (e.g., with a shaft support assembly 401 including one or more deflectable support elements 404, 406), actuation of the capacitor assembly 402 correspondingly moves the coupling shaft 306 as well as the probe tip 304 while the coupling shaft and the tip are laterally supported. Stated another way, the proximal and distal support element 404, 406 provide a moveable support structure that supports the shank 408 and the coupling shaft 306 and keeps the coupling shaft 306 relatively horizontal while at the same time facilitating movement of the probe tip 304 through actuation by the capacitor assembly 402. Similarly, where the transducer assembly 400 is moved and the capacitor assembly 402 is used in a passive configuration where actuation voltage is not applied across the capacitor assembly 402, the proximal and distal support springs 404, 406 provide lateral support to the shank 408 and the coupling shaft 306 while allowing at least one of the plates of the capacitor assembly 402 to move within the capacitor assembly 402 for measurement of displacement of the plate relative to the counter electrodes within the capacitor assembly 402.

Optionally, the coupling shaft 306 is supported at one or more locations (beyond the support provided by the capacitor assembly 402). For instance, a single support element 404, 406 (e.g., support spring) is coupled with the coupling shaft 306. In one example, the distal support element 406 is coupled between the coupling shaft 306 and the transducer housing 308. The distal support element 406 cooperates with the capacitor assembly 402 to support the coupling shaft 306 in a similar manner to support with distal and proximal support springs. For example, the distal support element 406 provides lateral support while allowing some lateral movement of the tip 304 and the shaft 306 (according to actuation of the capacitor assembly 402, piezo actuated movement of the tip 304 across a sample and the like) and the distal support element 406 assists in maintaining the coupling shaft 306 near horizontal to prevent saturation of the capacitor assembly 402.

In another example, the proximal support element 404 (e.g., support spring) is provided and spaced from the capacitor assembly 402. The proximal support element 404 supports the coupling shaft 306 in a similar manner to the distal support element 406 (but from an opposed side of the capacitor assembly 402). In still another example, three or more deflectable support elements are coupled along the coupling shaft 306. For example, two distal support elements like support element 406 are coupled distally along the coupling shaft 306 relative to the capacitor assembly 402. Optionally, one or more proximal support elements like support element 404 are coupled along the shaft 306 proximal to the capacitor assembly 402. The support elements 404, 406 (one, two, three or more springs and the like) are selectively coupled along the coupling shaft to provide lateral support to the coupling shaft, for instance to maintain the shaft in a substantially horizontal orientation, while at the same time facilitating lateral movement of the shaft 306 and the tip 304 according to their deflectable configurations (e.g., lateral movement caused through actuator operation and forces transmitted to the probe tip 304). The one or more movable support elements thereby allow for tuning of the lateral stiffness (i.e., support) of the coupling shaft 306 according to the length of the shaft, the configuration of the shaft within the transducer assembly 400, and the desired lateral stiffness and corresponding range of motion for the shaft.

Referring to FIGS. 4A and 4B again, the proximal and distal support elements 404, 406, for instance springs, as previously described provide lateral support to the shank 408 of the coupling shaft 306 and position the coupling shaft 306 at a substantially horizontal orientation where the transducer assembly 400 is positioned within an instrument such as a scanning or transmission electron microscope with a vertical electron beam 212 relative to the mechanical testing instrument 200 as shown in FIG. 2B. The proximal and distal support elements 404, 406 are positioned between one or more spring plates 410. As shown in FIGS. 4A and 4B, the spring plates 410 are positioned on either side of the proximal and distal support elements 404, 406 to assist in maintaining the proximal and distal support elements at a desired location along the shank 408 while at the same time providing a robust anchor for coupling of the proximal and distal support elements 404, 406 to the transducer body 308. A gap 414 is provided between each of the spring plates 410 and the shank 408 of the coupling shaft 306. The gap 414 between each of the spring plates 410 and the shank 408 ensures the coupling shaft 306 is supported entirely by the proximal and distal support elements 404, 406 and thereby able to move laterally and normally when actuated by the capacitor assembly 402 or alternatively when the transducer assembly 400 is moved relative to a sample, for instance, with a second transducer such as a piezo transducer.

In another example, the proximal and support elements 404, 406 are themselves spaced from the spring plates 410 by one or more peripheral rings 412 extending around the periphery of the proximal and distal support elements. The peripheral rings 412 space the proximal and distal support elements prings 404, 406 from the spring plates 410 and allow for deflection of the proximal and distal support elements 404, 406 according to movement of the coupling shaft 306 and the probe tip relative to the transducer body 308.

The proximal and distal support elements 404, 406, such as support springs, as shown in FIGS. 4A, 4B provide lateral support to the coupling shaft 306, as described above. Materials and spacing of the proximal and distal support elements 404, 406 relative to the capacitor assembly 402 are chosen to provide a specified lateral stiffness (e.g., support) to the coupling shaft 306 and the probe tip 304 while at the same time allowing displacement of the coupling shaft 306 and the probe tip 304, for instance, through actuation of the capacitor assembly 402. As described in further detail below, in one example the proximal and distal support elements 404, 406 are constructed with, but not limited to, beryllium copper, steel, titanium and ceramics, such as silicon, and the like. The proximal and distal support elements 404, 406 are spaced from about 0.1 to 100 millimeters from the capacitor assembly 402 to provide the specified lateral stiffness to the coupling shaft 306 and the probe tip 304 while at the same time allowing for displacement of the coupling shaft 306 and probe tip 304 relative to the transducer body 308 through deflection of the support elements. In one example, the proximal and distal support elements are spaced 4 millimeters from the capacitor assembly 402.

In another example, the proximal and distal support springs 404, 406 are constructed with, but not limited to, spring steels, titanium, ceramics, metals, combinations of the same and the like. The materials and spacing of the proximal and distal support springs 404, 406 are chosen to facilitate the movement of the coupling shaft 306 and the probe tip 304 through actuation by the capacitor assembly 402 (or through movement of the transducer assembly 400 through a second transducer such as a piezo transducer) while at the same time substantially horizontally positioning the coupling shaft 306 and probe tip 304 with a minimum of deflection due to gravity, mechanical noise, and the like. By maintaining the probe tip 304 and the coupling shaft 306 at a near horizontal (neutral or null) position while the transducer assembly 400 is positioned within an instrument, the capacitor assembly 402, for instance, a center plate of the capacitor assembly, is not appreciably displaced by gravity acting on the coupling shaft 306. This substantially prevents saturation of the capacitor and facilitates accurate measurement of displacement and forces incident on the probe tip 304. Further, the enhanced lateral stiffness minimizes undesirable movement of the probe tip 304 and coupling shaft 306 caused by mechanical noise and thereby ensures reliable sensing of displacement and force at the probe tip.

As previously described, FIGS. 4A and 4B show one example of a capacitor assembly 402 positioned within the transducer body 308 of the transducer assembly 400. The capacitor assembly 402 is configured in one example to provide actuation forces to the coupling shaft 306 and the probe tip 304 attached with the shaft. In another example, the capacitor assembly 402 is configured to measure displacement and forces incident on the probe tip 304. Optionally, the capacitor assembly 402 is configured for both actuation and measurement of displacement and forces (including torque) and the like incident on the coupling shaft 306 and the probe tip 304.

Figure 5A:
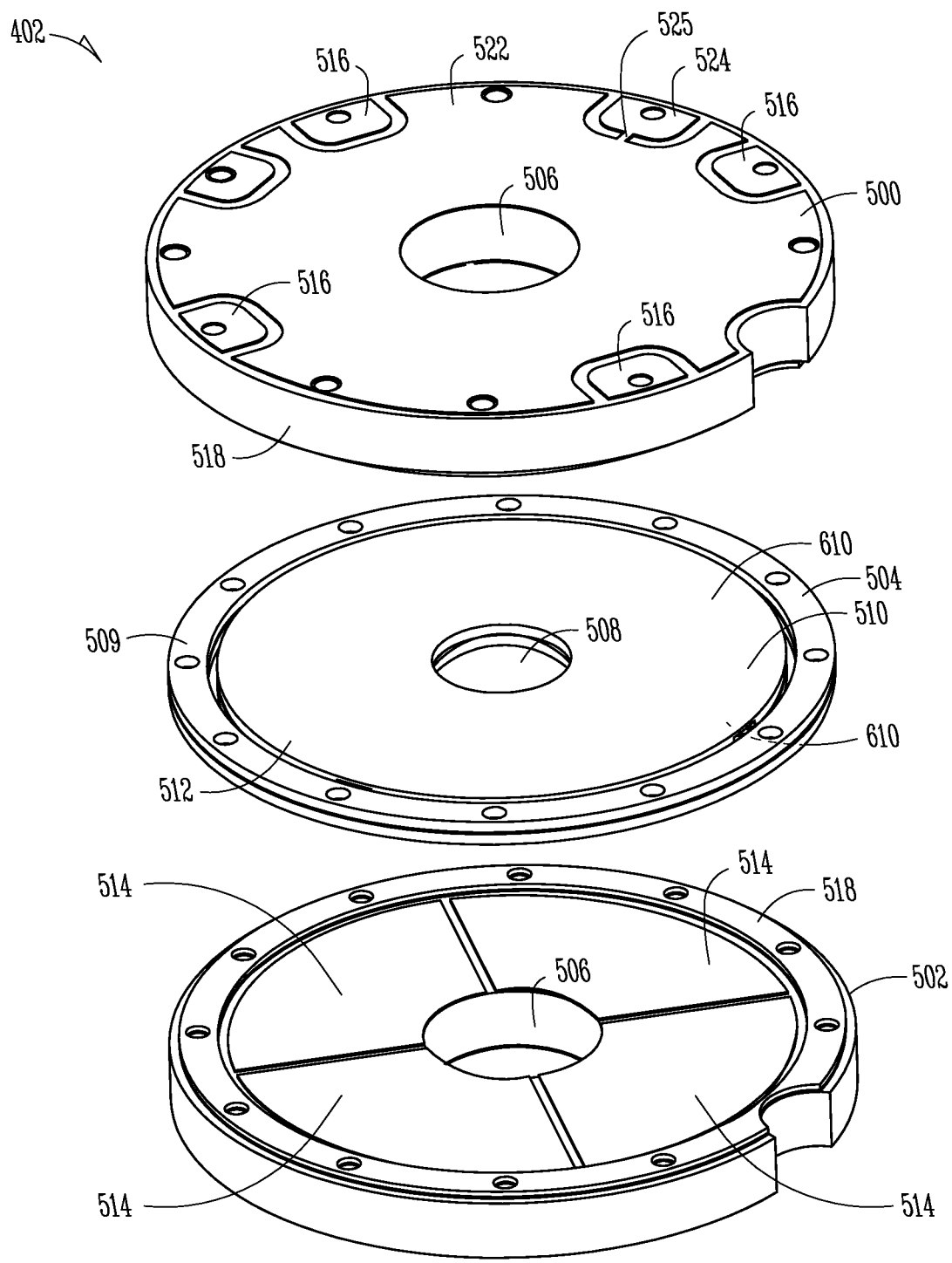
FIG. 5A is a partially exploded view of one example of a three dimensional transducer used with the mechanical testing instrument shown in FIG. 3.
Figure 5B:
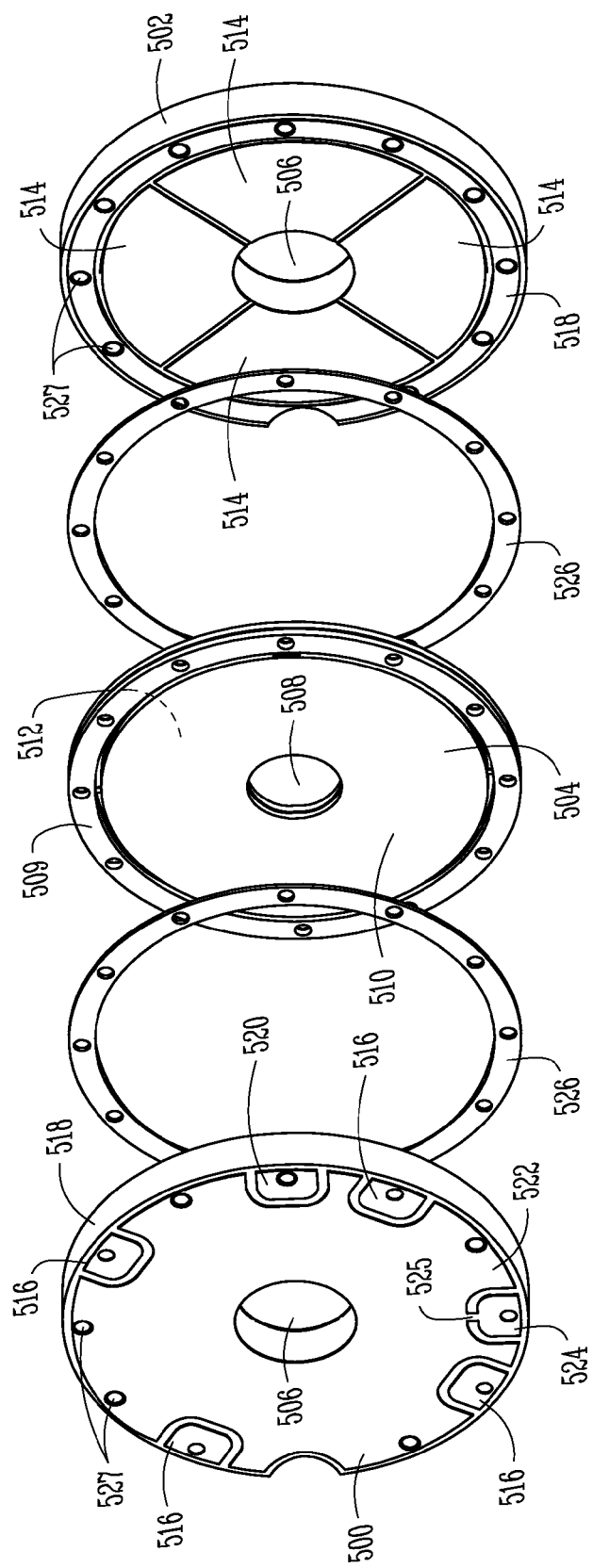
FIG. 5B is a partially exploded view of the three dimensional transducer shown in FIG. 5A.

Referring now to FIGS. 5A and 5B, one example of the capacitor assembly 402 is shown in two exploded views. The capacitor assembly 402 includes a capacitor having a three plate configuration. In another example, the capacitor assembly 402 includes a two plate configuration (i.e., where one of the plates is coupled with the shaft 306 and the opposed plate is coupled with the transducer body 308). In the example shown in FIGS. 5A and 5B, the capacitor assembly 402 includes a first counter electrode 500, a second counter electrode 502, and a center electrode assembly 504 positioned therebetween. Each of the first and second counter electrodes 500, 502 includes holes 506. The holes 506 are sized and shaped to position the shank 408 of the coupling shaft 306 therein and have space for X, Y motion of the coupling shaft 306 without the shaft touching the hole 506 side walls. As shown, for instance, in FIGS. 4A and 4B, the shank 408 is spaced away from each of the first and second counter electrodes 500, 502 (the counter electrodes are shown in an assembled configuration in FIGS. 4A and 4B).

The center electrode assembly 504 of the capacitor assembly 402 includes a center electrode orifice 508 sized and shaped to receive the shank 408 of the coupling shaft 306 therein. The center electrode orifice 508 is sized and shaped to engage the center electrode assembly 504 with the shank 408 as shown in FIGS. 4A and 4B (for instance, the shank 408 includes a recess or flange 416 sized and shaped to engage with the center electrode assembly 504). By engaging the center electrode assembly 504 with the shank 408 as shown in FIGS. 4A and 4B, movement of the coupling shaft 306 and the probe tip 304 is correspondingly transmitted to the center electrode assembly 504. Conversely, because of the engagement movement, such as actuation of the center electrode assembly 504, is transmitted from the center electrode assembly to the shank 408, the coupling shaft 306 and the probe tip 304.

The center electrode assembly 504 further includes upper and lower plates 510, 512 on opposed surfaces of the electrode assembly. As will be described in further detail below, each of the upper and lower plates 510, 512 provides a continuous surface within the transducer body 308 to fill substantially all of the cross-sectional area of the transducer body 308 and thereby maximize the sensitivity of the capacitor assembly 402 (including, for instance, sensitivity to displacement voltage changes as well as facilitating application of maximized torques and forces to the center electrode assembly and the attached coupling shaft 306 and probe tip 304).

As will be further described below, the center electrode assembly 504, including the upper and lower plates 510, 512, are suspended within a center electrode ring 509 surrounding the upper and lower plates 510, 512. The center electrode ring 509 supports the center electrode assembly 504 and facilitates the deflection of the upper and lower plates 510, 512, for instance, for actuation and measurement of displacement. Additionally, the center electrode ring 509 provides an electrical contact for measurement of output signals from the center electrode assembly 504 during operation of the mechanical testing instrument 300 and the nanomechanical test system 100 (See FIGS. 1, 3, 4A, and 4B).

Referring again to FIGS. 5A and 5B, the capacitor assembly 402 further includes the first and second counter electrodes 500, 502. Each of the first and second counter electrodes 500, 502 includes a plurality of sections, for instance electrode quadrants 514. In the example shown in FIGS. 5A and 5B, the first and second counter electrodes 500, 502 include four separate quadrants each. In another example, the first and second counter electrodes 500, 502 include two or more sections. Each of the electrode quadrants 514 is electrically isolated from the other electrode quadrants 514. Each of the electrode quadrants 514 is configured to transmit a different excitation signal to the center electrode assembly 504. As previously described, the transducer assembly 400 including the capacitor assembly 402 is configured for normal and lateral movement and measurement of forces and displacement normally and laterally. Stated another way, the transducer assembly 400 is configured for three dimensional (3D) actuation and measurement of forces and displacement. By transmitting different excitation signals through each of the electrode quadrants 514, normal as well as lateral (side to side) movement of the probe tip 304 is achieved. Further, as described below output signals based on one or more of the excitation signals from the counter electrode quadrants 514 and displacement of the center electrode assembly 504 are used to measure displacement of the tip 304 and forces incident on the tip 304 in three dimensions.

Each of the first and second counter electrodes 500, 502 includes a plurality of quadrant contacts 516 corresponding to the number of electrode quadrants 514. As shown in FIGS. 5A and 5B, each of the first and second counter electrodes 500, 502 includes the quadrant contacts 516 on an opposed surface relative to the electrode quadrants 514. In another example, the quadrant contacts 516 are provided on another surface of the first and second counter electrodes, for instance, the periphery or peripheral edge of the electrodes.

Additionally, in the example shown, the first and second counter electrodes 500, 502 each include guard rings 518 circumscribing the perimeter of the electrode quadrants 514. The guard rings 518 receive guard signals from the electronics of the mechanical testing instrument 200 to protect the input signals to the first and second counter electrodes 500, 502 as well as the output signals from the displaceable center electrode assembly 504. In a similar manner to the quadrant contacts 516, the guard rings 518 include guard ring contacts 520 on opposed surfaces of the first and second counter electrodes 500, 502. The guard ring contacts 520 provide electrical contacts for reception of the guard signals and transmission of the guard signals to the guard rings 518.

Additionally, the first and second counter electrodes 500, 502 in the examples shown in FIGS. 5A and 5B include respective ground planes 522 extending across surfaces opposed to the electrode quadrants 514. The ground plane 522 includes an electrical contact such as a ground plane contact 524 in a similar manner to the quadrant contacts 516 and guard ring contacts 520. As best shown in FIG. 5B, the ground plane contact 524 is electrically coupled with the ground plane 522 with a bridge 525 extending therebetween. The quadrant contacts 516 and the guard ring contacts 520 are coupled with the respective features (e.g., guard ring and quadrants) on the opposed surfaces of the first and second counter electrodes 500, 502. Electrical connections are in one example provided through pass-through holes 527 (e.g., plated through holes) extending around the periphery of the first and second electrode contacts. Alternatively, wrap-around contacts are used that bridge between each of the quadrant contacts 516, guard ring contacts 520, and their corresponding features on the opposed surfaces of the first and second counter electrodes 500, 502.

Referring now to FIG. 5B, the capacitor assembly 402 in another example includes one or more dielectric rings 526 interposed between the counter electrodes 500, 502 and the center electrode assembly 504. The dielectric rings 526 space the center electrode assembly 504 from the first and second counter electrodes 500, 502 and substantially prevent contact between the upper and lower plates 510, 512 and the first and second counter electrode quadrants 514. That is to say, the dielectric rings 526 define the plate gap between the center electrode assembly 504 and the electrode quadrants 514 of the first and second counter electrodes 500, 502. In one example, the dielectric rings provide a space between the center electrode assembly 504 and the first and second counter electrodes 500, 502 of around 70 microns on either side of the center electrode assembly 504. The gap between the center electrode assembly and the first and second counter electrodes is around 10 nanometers to 1 millimeter in another example. Because capacitance is one of the electrical values measured to determine force and displacement of the probe tip 304 (see FIGS. 3, 4A, 4B), a minimal gap between the first and second counter electrodes 500, 502 and the center electrode assembly 504 is desired (capacitance is inversely proportional to the plate gap between the electrodes). Stated another way, with a larger capacitance value of the capacitor assembly 402, partly due to a minimal plate gap, changes in capacitance due to displacement are correspondingly larger and provide increased sensitivity for to displacement measurements.

Figure 6:
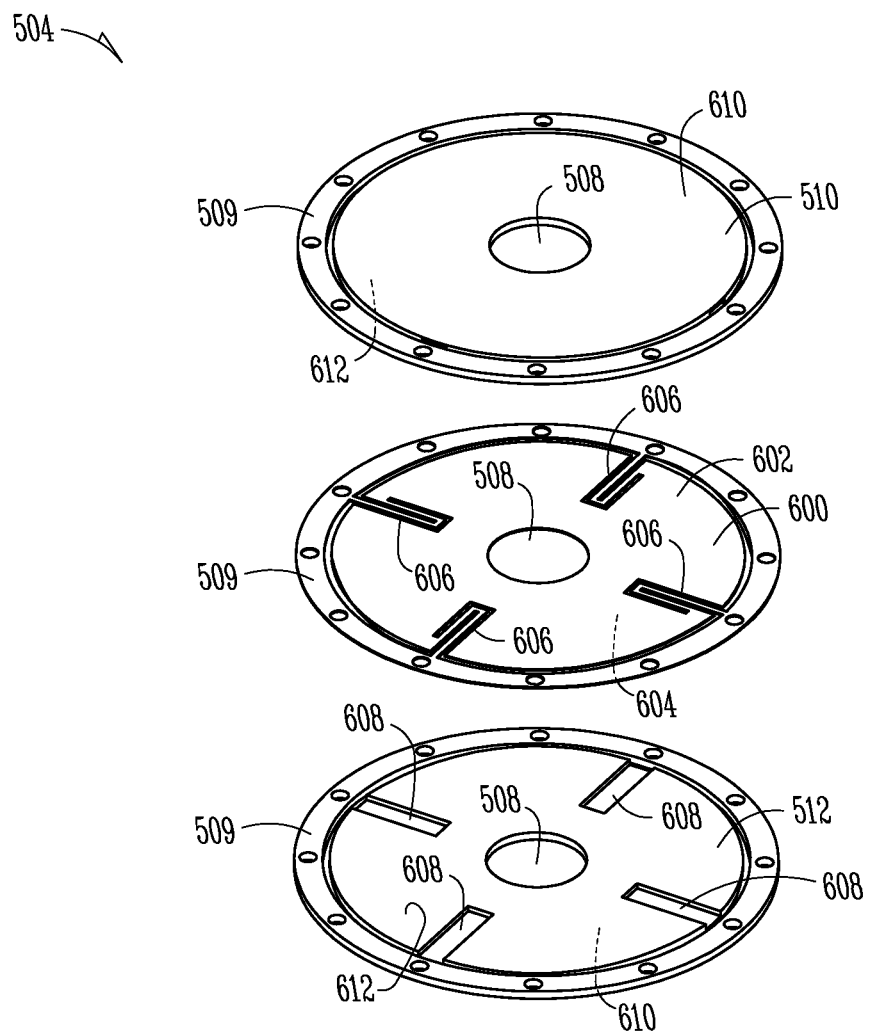
FIG. 6 is an exploded view of one example of a center electrode assembly used in the three dimensional transducer shown in FIG. 5A.

FIG. 6 shows an exploded view of the center electrode assembly 504 shown in FIGS. 5A and 5B. The center electrode assembly 504 includes the upper plate 510 and the lower plate 512. A center plate 600 is coupled between the upper and lower plates 510, 512. As shown in FIG. 6, the center plate 600 includes a first surface 602 directed toward the upper plate 510 and a second surface 604 opposed to the first surface 602 and directed toward the lower plate 512. When assembled, the first and second surfaces 602, 604 engage along the upper and lower plates 510, 512 respectively. The upper and lower plates 510, 512 and the center plate 600 thereby provide a unitary assembly configured to move within the capacitor assembly 402. That is to say, the upper and lower plates 510, 512 are affixed to the center plate 600, and when the center electrode assembly 504 is moved (e.g., through actuation voltage or deflection caused by movement of the tip through a second actuator) the upper and lower plates 510, 512 and the center plate 600 move as a single unit.

Referring again to FIG. 6, the center electrode assembly 504 further includes one or more plate springs 606 coupled between the center plate 600 and the center electrode ring 509. As shown in FIG. 6, the center electrode ring 509 in at least one example is split between the upper and lower plates 510, 512 as well as the center plate 600. In the example shown, the plate springs 606 are coupled between the center plate 600 and the center electrode ring 509 associated with the center plate 600. In one example, the plate springs 606 are formed as part of the center plate 600 and thereafter machined out of the center plate 600. In another example, the plate springs 606 are etched from the center plate 600. Optionally, the plate springs 606 as well as the center plate 600 and the center electrode ring 509 are constructed with but not limited to beryllium copper, spring steel, and the like.

In the example shown in FIG. 6, the upper and lower plates 510, 512 include spring recesses 608 formed in the upper and lower plates 510, 512 to facilitate the deflection of the plate springs 606 during movement of the center electrode assembly 504. The spring recesses 608 are sized and shaped within the upper and lower plates 510, 512 to facilitate free movement of the plate springs 606 without engagement with either of the upper or lower plates 510, 512. As to shown in FIG. 6, the spring recesses 608 are formed in the concealed faces 612 of each of the upper and lower plates 510, 512 (the spring recesses 608 of the upper plate 510 are concealed by the exposed face 610). The exposed faces 610 of the upper and lower plates 510, 512 correspond to the exposed portions of the center electrode assembly 504 shown in FIGS. 5A and 5B and form continuous unbroken electrode surfaces. That is to say, the upper and lower plates 510, 512 conceal the plate springs 606 as well as the spring recesses 608 therein and provide a continuous electrode surface for the center electrode assembly 504 extending from the center electrode orifice 508 to the center electrode ring 509 adjacent to the inner wall of the transducer body 308. (See FIGS. 4A, 4B). As will be described in further detail below, by concealing the plate springs 606 within the spring recesses 608 with the overlying exposed faces 610 of the upper and lower plates 510, 512, the critical area of the center electrode assembly 504 is maximized to thereby correspondingly maximize the sensitivity and force and torque output of the capacitor assembly 402.

Figure 7:
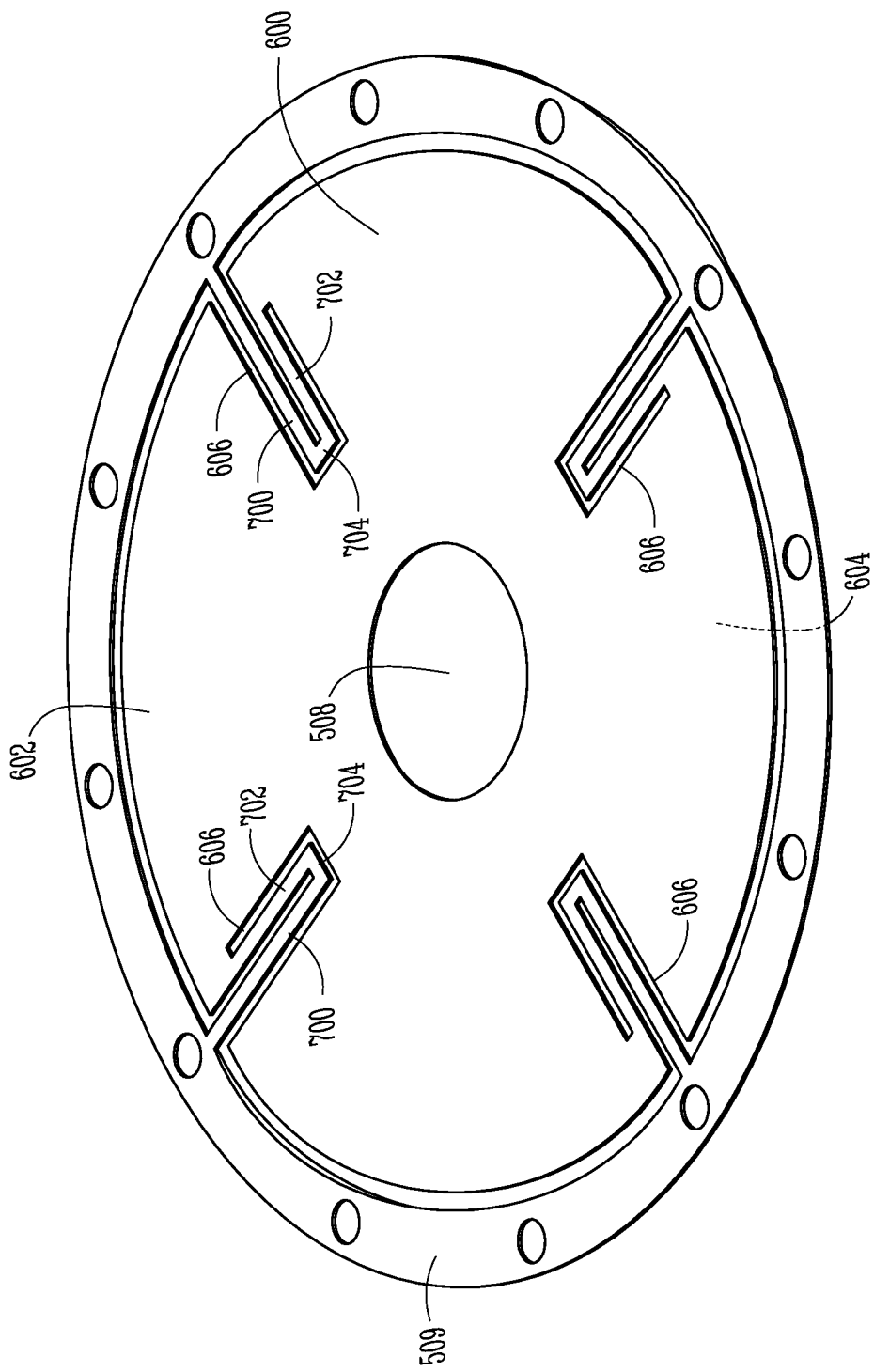
FIG. 7 is a perspective view of one example of the center plate of the center electrode assembly shown in FIG. 6.

Referring now to FIG. 7, one example of the center plate 600 shown in FIG. 6 is provided. The center plate 600 includes the features previously described in FIG. 6, such as a first surface 602 and an opposed second surface 604 as well as the plate springs 606. As previously described, the center plate 600 is configured for positioning between the upper and lower plates 510, 512 and is engaged therebetween. The center plate 600 thereby suspends the upper and lower plates 510, 512 within the center electrode ring 509 and allows for movement of the assembly of the center plate 600 and the upper and lower plates 510, 512 according to actuation voltages provided by one or more of the first and second counter electrodes 500, 502 or displacement caused by engagement of the probe tip 304 with the sample for instance through a piezo actuator.

As shown in FIG. 7, the plurality of plate springs 606 are disposed radially around the center plate 600. As shown in FIG. 7, the plate springs 606 are in one example positioned at around 90-degree positions relative to each other. In other examples, one or more plate springs 606 are provided on the center plate 600 for suspension of the center plate relative to the center electrode ring 509. For instance, where two plate springs 606 are provided in one example, the plate springs are positioned at 180-degree intervals relative to each other. The plate springs 606 shown in FIG. 7 include multiple spring arms 700, 702 with one or more elbows 704 extending therebetween. As shown in the example of FIG. 7, the plate springs 606 include a first spring arm 700 coupled with the center electrode ring 509 and a second spring arm 702 coupled with the center plate 600. The elbow 704 is coupled between each of the first and second spring arms 700, 702 and thereby provides a flexible joint that cooperates with the first and second spring arms 700, 702 to increase the length of the springs. By increasing the length of the plate springs 606 the spring stiffness of the springs is reliably maintained over an entire range of deflection of the center electrode assembly 504. Stated another way, the spring stiffness of the plate spring 606 is consistent over a range of deflections in part because of the length of the spring. Further, the spring stiffness is substantially the same at the maximum displacement of the center electrode assembly (e.g., prior to one or more of engagement between the center electrode and the counter electrodes 500, 502 or engagement of the plate springs 606 with the upper and lower plates 510, 512) relative to negligible displacement of the center electrode assembly near a neutral or rest position. The plate springs 606 thereby provide consistent and predictable support to the center electrode assembly 504 throughout deflection of the center plate 600 and upper and lower plates 510, 512 coupled with the center plate 600.

Referring back to FIG. 6, the spring recesses 608 associated with each of the plate springs 606 are sized and shaped to receive each of the plate springs 606 during deflection of the plate springs 606 through operation of the capacitor assembly 402. For instance, as the center electrode assembly 504 deflects laterally, normally, rotates, and the like, the plate springs 606 correspondingly deflect within the spring recesses 608. The spring recesses 608 are sized and shaped according to the size of the plate springs 606 as well as the spring materials to ensure that the plate springs 606 in the deflected states do not engage with the upper and lower plates 510, 512. The center electrode assembly 504 is thereby able to freely deflect within the center electrode ring 509 without otherwise impinging on one or more of the upper and lower plates 510, 512. That is to say, that spring recesses 608 substantially prevent any constraint of deflection of the plate springs 606 during movement of the center electrode assembly 504, for instance, under a maximum torque load or force load as provided through actuation voltages applied by the electronics of the nanomechanical test system 100. Stated another way, the upper and lower plates 510, 512 with the spring recesses 608 cooperate with the center plate 600 to suspend the plate springs 606 within the volume defined by the recesses and thereby substantially prevent the physical constraint of the deflection of the plate springs during actuation of the center electrode assembly 504 whether by an actuation voltage or engagement and movement of the probe tip 304 with a sample.

As previously described above, the capacitor assembly 402 including the center electrode assembly 504 and opposed first and second counter electrodes 500, 502 provide capacitor plates having a maximized area within the transducer body 308. For instance, as previously described, the center electrode assembly 504 includes an upper plate 510 and lower plate 512 that substantially conceal the plate springs 606 coupled with the center plate 600 therein. By concealing the plate springs 606, each of the upper and lower plates 510, 512 provides a uniform continuous surface extending from the center electrode orifice 508 to the center electrode ring 509 immediately adjacent to the transducer body 308. Because the center electrode assembly 504 is able to utilize nearly the entire space of the cross-sectional area of the transducer body 308, the first and second counter electrodes 500, 502 similarly extend across the same corresponding area of the center electrode assembly 504. Stated another way, the first and second counter electrodes 500, 502 utilize substantially all of the cross-sectional area of the transducer body 308 from the holes 506 to the guard rings 518. By concealing the plate springs 606 the plate overlapping area between the center electrode assembly 504 and the first and second counter electrodes 500, 502 is maximized.

Further, the enhancement of the overlapping area of the electrodes is provided at the periphery of the electrodes near the transducer body 308 inner wall. As the area added is nearer the periphery of the transducer body 308, the enhanced area provides enhanced generation of electrostatic forces based on the increased area and moment arm provided at the peripheral edges of the electrodes 500, 502, 504. That is to say, the increased area at the periphery of to the electrodes leverages even greater generation of electrostatic forces, for instance, a greater maximum force and greater maximum torque relative to previous capacitor assembly designs having the electrodes positioned toward the interior of the transducer body and recessed away from the transducer body interior walls.

The increase in the overlapping area of the first and second counter electrodes 500, 502 with the center electrode assembly 504 increases the capacitance of the capacitor assembly 402. Capacitance is proportional to area and inversely proportional to the gap between the electrodes. Having a larger capacitance relative to previously designed capacitor assemblies provides a correspondingly larger capacitance gradient to normal and lateral displacement. Stated another way, the capacitor assembly 402 described herein provides larger measurable changes in capacitance caused by displacement and thereby has increased sensitivity to such displacement. For instance, in one example, capacitance is determined by the relationship:

$$C = \varepsilon \cdot \frac{A}{d}$$

C is equal to capacitance and $\varepsilon$ is the relative static permittivity or dielectric constant of the material such as air between the first and second counter electrodes 500, 502 and the center electrode assembly 504. As shown in the relationship, capacitance is directly proportional to the area of the overlapping plates such as the first and second counter electrodes 500, 502 and the center assembly 504 and is inversely proportional to the distance or plate gap (d) between the electrodes. As previously described herein, the capacitor assembly 402 extends over a relatively large area within the transducer body 308 (e.g., between the shaft 306 and the transducer body 308 inner wall) and based on the relationship between area (A) and the plate gap (d) even small changes in the gap between the electrodes create large, easily measurable changes in the capacitance (i.e., increased sensitivity).

Further, the increased overlapping area between the center electrode assembly 504 (because of its continuous unbroken surface across the upper and lower plates 510, 512) cooperates with the similarly unbroken surface of the electrode quadrants 514 of the first and second counter electrodes 500, 502 to facilitate the generation of greater maximum force and moment values relative to other previous designs. For instance, as previously discussed above, capacitance is directly proportional to the overlapping area between the electrodes 500, 502, 504. Similarly, the force generated through a particular actuation voltage is directly proportional to the capacitance value. Because of this relationship as the overlapping area of the electrodes increases, the capacitance increases, and the maximum force capable of being generated with a particular actuation voltage is similarly increased. One example of relation of electrostatic force as it relates to capacitance is provided with the equation below:

$$F = C \cdot \frac{V^2}{2d}$$

As shown in this relationship, as the capacitance value increases (e.g., through increased overlapping area between electrodes), the corresponding force increases for a set actuation voltage. The capacitor assembly 402 of the transducer assembly 400 shown in FIGS. 4A and 4B is thereby able to leverage the maximized overlapping area of the first and second counter electrodes 500, 502 with the center electrode assembly 504 to correspondingly maximize the capacitance and maximum force values generated through actuation voltages applied to the capacitor assembly 402. Further, because the area added to the capacitor assembly 402 is at the periphery of the electrodes 500, 502, 504 the torque generated with the capacitor assembly is maximized. For example, the moment arm at the periphery of the capacitor assembly 402 (e.g., at the peripheral edges of the first and second counter electrodes 500, 502 and the center electrode assembly 504) is greater immediately adjacent to the transducer body 308 as shown in FIG. 3 as compared to the interior portions of the capacitor assembly. Being able to generate electrostatic forces at the periphery of the first and second counter electrodes 500, 502 and the center electrode assembly 504 with the greater peripheral moment arm maximizes the torque generated at the capacitor assembly 402.

In one example, the capacitor assembly 402 includes an overlapping electrode area of 36.2 square millimeters where the first and second counter electrodes 500, 502 include four electrode quadrants 514 each. A nominal electrode gap (the plate gap between the first and second counter electrodes 500, 502 and the center electrode assembly 504) in one example is around 1 nanometer to 1 millimeter, for instance 70 microns. With this area and this nominal electrode gap, the nominal capacitance in a neutral orientation for the capacitor assembly 402 is approximately 4.4 picofarads (pF). Stated another way, each one of the electrode quadrants 514 and the corresponding portions of the center electrode assembly 504 has a nominal capacitance of approximately 1.1 pF. In some designs without the features described herein, the nominal capacitance of the entire capacitor assembly was approximately 1.0 pF. Stated another way, the capacitor assembly 402 of the transducer assembly 400 has a nominal capacitance at least four times as large as that of previous designs. In this exemplary capacitor assembly 402, the capacitance gradient to displacement at the nominal gap (or 70 microns) in the normal direction (along the Z axis) is approximately 28 femtofarads per micron for four quadrants on each of the first and second counter electrodes 500, 502. In contrast, other designs without the features described herein included a capacitance gradient at the nominal gap in the normal direction of approximately 7.2 femtofarads per micron. The exemplary designs provided herein thereby provide a fourfold increase in sensitivity in the normal direction.

In another example, the capacitor assembly 402 described herein for the transducer assembly 400 provides a nominal capacitance gradient for displacement in the lateral direction (the X and Y axes) of around 1.4 femtofarads per micron assuming the actuation of two electrode quadrants 514 on each of the first and second counter electrodes 500, 502. In contrast, a prior design includes perhaps one fifth that sensitivity or, in one example, an approximate sensitivity of 0.26 femtofarads per micron. The transducer assembly 400 including the capacitor assembly 402 thereby has a sensitivity along the lateral axes approximately five times greater than that of previous designs.

Additionally, the center electrode assembly configuration 504 with the upper and lower plates 510, 512 extending over and substantially concealing the plate springs 606 prevents electrostatic interaction of the springs with the counter electrodes 500, 502. Concealing the springs 606 with the upper and lower plates 510, 512 prevents the springs 606 from interaction with electrostatic forces during operation of the transducer assembly 400 since the springs 606 are covered with the upper and lower plates 510, 512 which are part of the same electrode.

Figure 8:
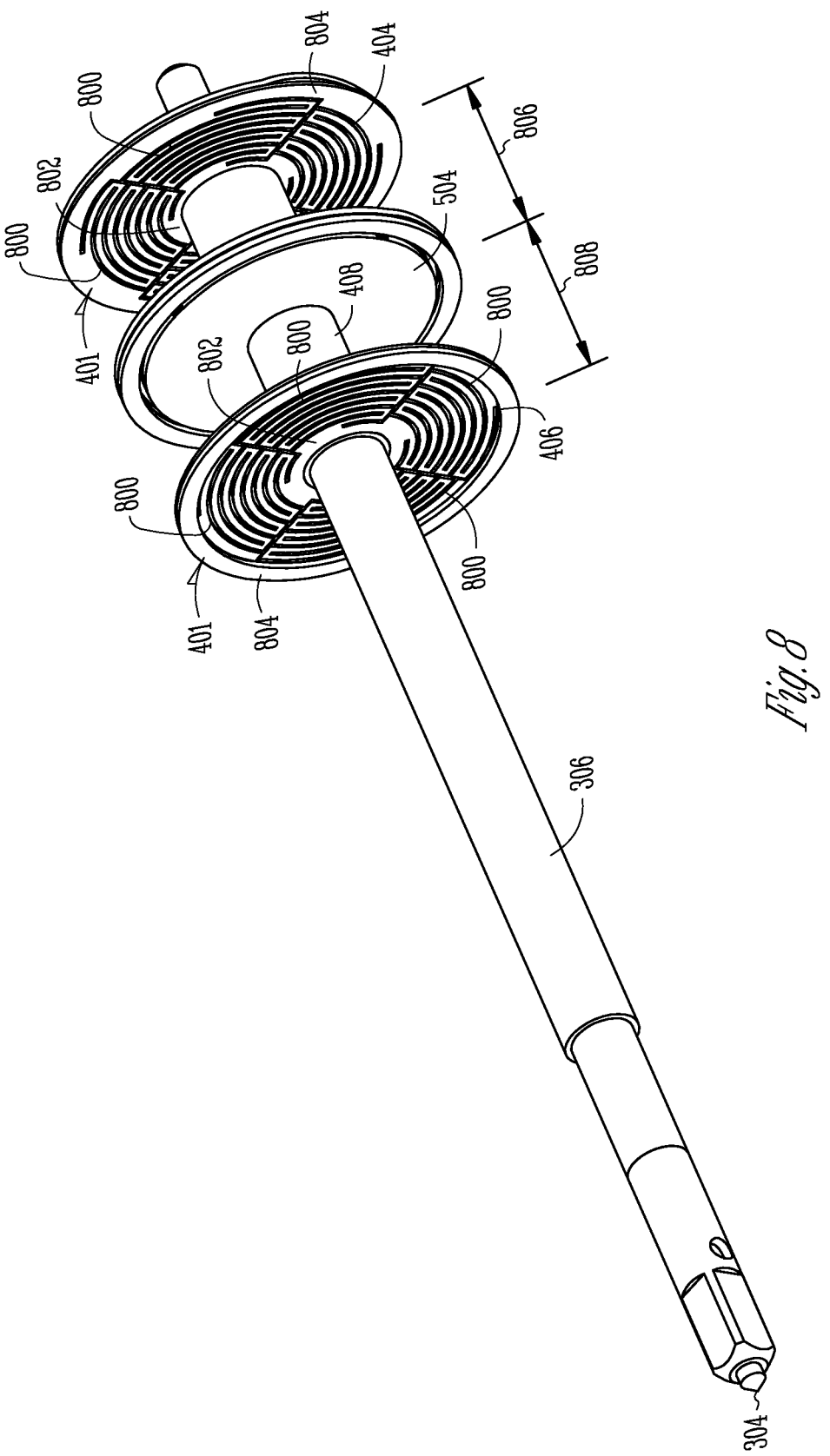
FIG. 8 is a perspective view of the mechanical testing instrument shown in FIG. 4A including proximal and distal support elements.

FIG. 8 shows portions of the transducer assembly 400 shown in FIGS. 4A and 4B. For instance, the view shown in FIG. 8 shows the coupling shaft 306 as well as the shank 408 positioned within the center electrode assembly 504 with the proximal and distal support elements 404, 406 (e.g., support springs) spaced from the center electrode assembly as previously described. The spring plates 410 and the first and second counter electrodes 500, 502 (shown and described previously) are removed from this view to expose the proximal and distal support elements 404, 406. As shown in FIG. 8, each of the proximal and distal support elements 404, 406 are spring elements and in one example include a plurality of spring elements 800 extending radially around the coupling shaft 306. This will be described in further detail below. The plurality of spring elements 800 of each of the proximal and distal support elements 404, 406 provides consistent and predictable lateral support around the coupling shaft 306 to maintain the coupling shaft 306 and the probe tip 304 at a substantially horizontal orientation relative to gravity (e.g., the coupling shaft 306 is deflected from horizontal a slight amount by gravity, such as a 12 micron offset displacement of the tip 304). As shown in FIG. 8, each of the spring elements 800 in the example extend around the shank 408 at approximately 90 degree arcs each. In other examples, the proximal and distal support springs 404, 406 include but are not limited to one or more spring elements 800 extending completely or partially around the shank 408.

Referring again to FIG. 8, the spring elements 800 extend between a spring hub 802 positioned adjacent to the shank 408 of the coupling shaft 306 and a spring rim 804 sized and shaped for coupling between the spring plates 410 shown in FIGS. 4A and 4B. In one example, the spring rims 804 provide a raised surface from the spring elements 800 of the proximal and distal support springs 404, 406 for engagement with the spring plates 410 to facilitate the displacement of the spring elements 800 during movement of the coupling shaft 306 and the probe tip 304. Stated another way, the spring plates 410 are spaced a small amount away from the proximal and distal support elements 404, 406 to allow for the deflection of the spring elements 800 during movement of the coupling shaft 306. The spring plates 410 engage with the spring rims 804 to provide support to the proximal and distal support elements 404, 406 as well as a robust fitting for coupling with the transducer body 308 (see FIGS. 4A, 4B).

Referring again to FIG. 8, the proximal and distal support elements 404, 406 are positioned with respect to the center electrode assembly 504 (i.e., the capacitor assembly 402 shown in FIGS. 4A, 4B) according to proximal and distal spacing 806, 808. In one example, the proximal and distal spacing 806, 808 is identical. For instance, the proximal and distal support elements 404, 406 are positioned equidistantly from the center electrode assembly 504 of the capacitor assembly 402. In one example, the proximal and distal support elements 404, 406 are positioned around 4 millimeters from the center electrode assembly 504. In still another example, the proximal and distal support elements 404, 406 are spaced at different distances relative to the center electrode assembly 504. For instance, the distal support element 406 is positioned further from the center electrode assembly 504 and the proximal support element 404 is positioned relatively closer to the center electrode assembly 504 (i.e., the spacing 808 is larger than the spacing 806). Optionally, in another example, the proximal support element 404 is positioned further from the center electrode assembly 504 than the distal support element 406.

The proximal and distal support springs 404, 406 are spaced relative to the center electrode assembly 504 to maintain the coupling shaft 306 as well as the probe tip 304 coupled thereon at a substantially horizontal orientation as previously described. In another example, the proximal and distal support springs 404, 406 are positioned as provided relative to the center electrode assembly 504 to provide the lateral support for positioning of the coupling shaft 306 as previously described. Additionally, the proximal and distal support springs 404, 406 are constructed and spaced to allow the coupling shaft 306 and the probe tip 304 to deflect laterally and normally according to actuation voltages applied to the capacitor assembly 402 and forces and moments provided through the probe tip 304. That is to say, the proximal and distal support springs 404, 406 as constructed and positioned along the coupling shaft 306 provide lateral support to the coupling shaft 306 and the center electrode assembly 504 and substantially prevent saturation of the capacitor assembly 402 with displacement caused by gravity (i.e., artificial shrinking of the gap between plates caused by gravity as opposed to displacement caused through testing). The proximal and distal support springs 404, 406 also permit lateral movement of the coupling shaft 306 and the probe tip 304 with corresponding displacement of the center electrode assembly 504 of the capacitor assembly 402 to facilitate the consistent and reliable measurement of probe tip 304 displacement. Stated another way, the proximal and distal support springs 404, 406 provide lateral support to the coupling shaft 306 to substantially keep the coupling shaft 306 at a horizontal orientation while at the same time permitting movement of the coupling shaft 306 and one or more of deflection and movement of the center electrode assembly 504 to ensure displacement of the center electrode assembly 504 is readily measurable. Actuation voltages applied across the capacitor assembly 402 as well as forces incident on the probe tip 304, for instance, through actuation of the transducer assembly 400 through movement of a piezo actuator, are thereby measurable at the capacitor assembly 402 while the coupling shaft 306 is laterally supported.

In one prophetic example, the transducer assembly 400 is modeled and analyzed, for instance, through finite element analysis and the positions of the proximal and distal support springs 404, 406 are set at around 4 millimeters from the center electrode assembly 504. In this example, the lateral stiffness of the transducer assembly 400 including the coupling shaft 306 is around 71 newtons per meter, which is around a 20-fold increase from an unsupported shaft and successfully limits the provision of an uneven gap between the center electrode assembly 504 and the first and second counter electrodes 500, 502. For instance, in such an example the deflection of the coupling shaft 306 and the probe tip 304 from true horizontal is around 12 microns.

Figure 9:
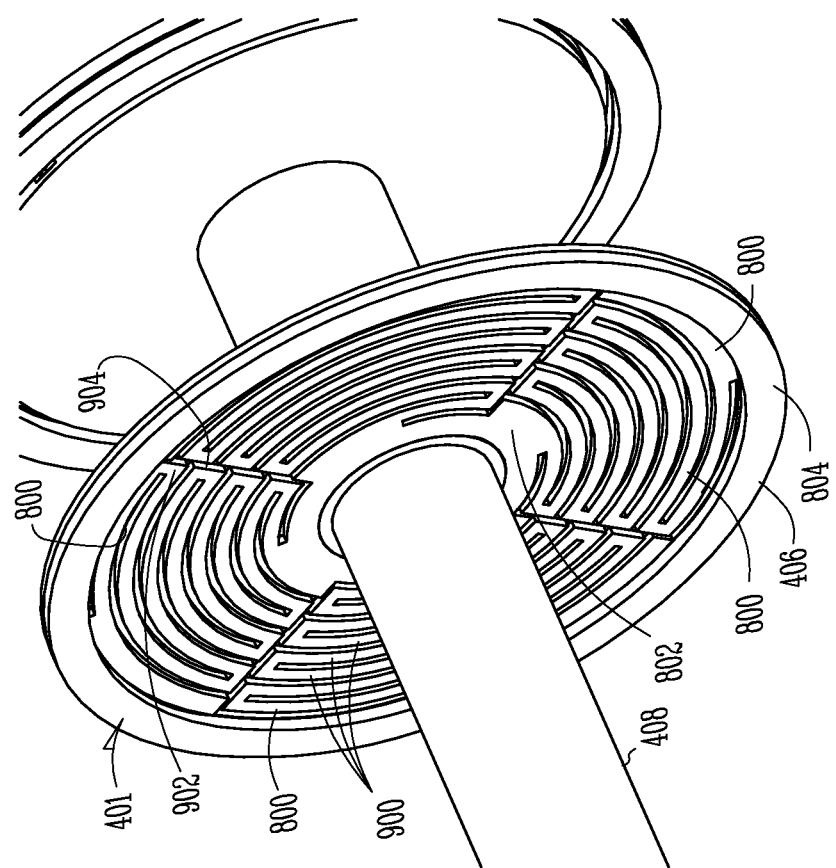
FIG. 9 is a perspective view of a support element coupled along a coupling shaft.

FIG. 9 shows a detailed view of the distal support element 406. In one example, the proximal and distal support elements 404, 406 are substantially identical and the description provided herein is applicable to the proximal support element 404. FIG. 9 provides a more detailed view of the distal support element 406 including its spring elements 800. As shown in FIG. 9, each of the spring elements 800 is comprised of one or more spring arms 900 extending arcuately relative to the coupling shaft shank 408 around the spring hub 802. As shown in FIG. 9, each of the spring arms 900 is coupled with adjacent spring arms through an elbow 902 extending therebetween. Although curved spring arms 900 are shown in FIG. 9, in another example the spring arms include, but are not limited to, arcuate-extending spring arms that are straight, curved, zigzagging or have other configurations. As previously described, the proximal and distal support elements 404, 406 include one or more spring elements 800. Where the elements include two or more spring elements 800 as shown in FIG. 9, they are separated by spring channels 904 formed in an otherwise continuous surface of the proximal and distal support springs 404, 406. In one example, the disks forming the proximal and distal support springs 404, 406 are machined to provide the spring channels 904 that define the individual spring elements 800 including the spring arms 900 and the elbows 902. Additionally, the spring channels 904 as shown in FIG. 9 delineate each of the spring elements 800 and separate the spring elements 800 between the spring hub 802 and spring rim 804.

As previously described above, in one example the spring arms 900 and elbows 902 are formed with machining of a continuous disk. In another example, the spring arms 900 and elbows 902 are formed with but not limited to etching, focused ion beam milling and other manufacturing techniques capable of forming spring arms 900 and elbows 902 for a transducer assembly 400 such as the transducer assembly 400 shown in FIGS. 4A and 4B.

The use of arcuate extending spring arms 900 extending between one or more elbows 902 as shown in FIG. 9 provides spring elements 800 that have a substantially greater length than other spring configurations such as leaf springs and the like extending from a spring hub to a spring rim. By using multiple spring arms 900 and elbows 902, the spring constant or stiffness of the elements 404, 406 does not appreciably change with deflection. Instead, the proximal and distal support elements 404, 406 provide consistent lateral support in all directions (e.g., throughout movement in the X and Y plane) because the spring elements 800 surround the shaft 306 (including the shank 408) and because the elements 800 have a relatively large length (relative to leaf springs). Stated another way, the support elements 404, 406, including for instance the spring elements 800, continuously extend around and support the coupling shaft 306. The continuous extension or surrounding of the coupling shaft 306 includes the support elements 404, 406 surrounding the coupling shaft even with negligible gaps, such as spring channels 904, between spring elements 800.

Because of their enhanced length (e.g., through arms and elbows), the spring elements 800 of the proximal and distal support elements 404, 406 provide consistent and predictable lateral support to the coupling shaft 306 and thereby provide predictable counter forces and moments to actuation of the coupling shaft 306 and the probe tip 304. Similarly, the proximal and distal support elements 404, 406 provide consistent and predictable counter moments and counter forces to forces applied to the coupling shaft 306 through the probe tip 304 (e.g., the probe tip is moved across a sample with an actuator such as a piezo actuator shown in FIG. 1 as a 3D coarse positioner 112 or 3D fine positioner 114).

Figure 10:
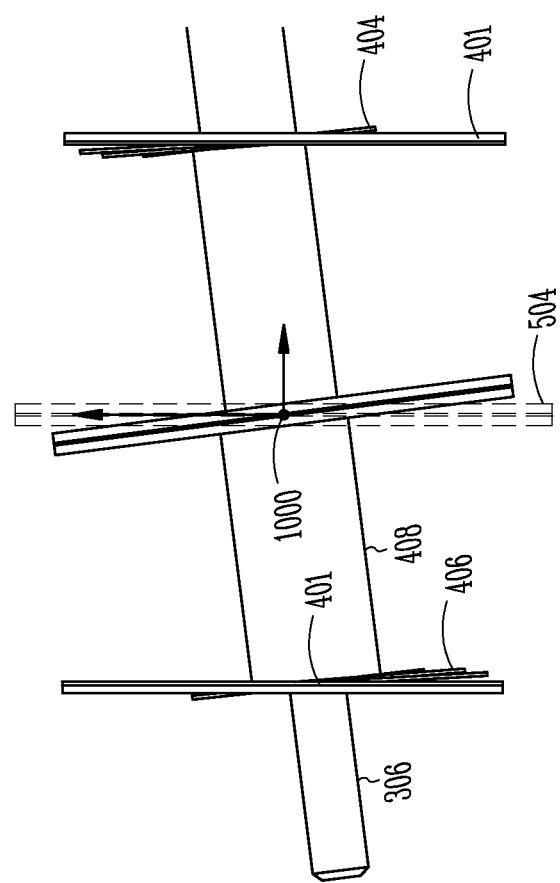
FIG. 10 is a schematic side view of the three dimensional transducer at the center of rotation.

FIG. 10 shows a schematic view of the coupling shaft 306 including the shank 408 coupled with the center electrode assembly 504 and the proximal and distal support elements 404, 406 (e.g., support springs). As previously described, the proximal and distal support elements 404, 406 provide lateral support to the coupling shaft 306 and position the coupling shaft 306 at a substantially horizontal position while the coupling shaft 306 is subject to gravity. Additionally, the proximal and distal support elements 404, 406 provide the lateral support for horizontal positioning while at the same time only increasing the lateral stiffness to a point that actuation voltages as well as physical engagement of the probe tip 304 with samples will deflect the center electrode assembly 504 thereby allowing for measurement of displacement of the coupling shaft 306 and probe tip 304 during testing procedures. Besides tuning the lateral stiffness of the coupling shaft 306 to provide each of these features (lateral support to the coupling shaft as well as facilitating deflection of the coupling shaft 306 when under a load), the proximal and distal support elements 404, 406 ensure the center of rotation 1000 is substantially coincident with the center electrode assembly 504.

The coupling shaft 306 is shown in a rotated state around a center of rotation 1000 and the center of rotation 1000 is shown substantially centered within the center electrode assembly 504. The proximal and distal support springs 404, 406 support the coupling shaft 306 as previously described, and the support provided by the elements 404, 406 artificially moves the center of rotation 1000 of the coupling shaft 306 including the shank 408 to the center of rotation 1000 as shown in FIG. 10. Stated another way, the proximal and distal support elements 404, 406 tune the center of rotation 1000 of the coupling shaft 306 to the position shown substantially aligned and centered with center electrode assembly 504. That is to say, the proximal and distal support elements 404, 406 provide radial support around the coupling shaft 306 and ensure that the coupling shaft 306 rotates around the center of rotation 1000 at the center electrode assembly 504 due to the counter forces and counter moments applied by the proximal and distal support elements 404, 406 during rotation and deflection of the coupling shaft 306.

By maintaining the center of rotation 1000 at the center electrode assembly 504, the center electrode assembly 504 is able to maximize the force and torque it may apply to the coupling shaft 306 resulting in a maximum range of displacement and rotation of the coupling shaft 306 and the probe tip 304 coupled with the coupling shaft 306. If the center of rotation 1000 were positioned away from the center electrode assembly 504 in at least some examples, the magnitude of displacement caused by actuation voltages across the capacitor assembly 402 (see FIGS. 4A, 4B) would be smaller as the moments and forces applied through the capacitor assembly 402 at the center electrode assembly 504 engaged with the shank 408 would be positioned away from the center of rotation of the coupling shaft 306. That is to say, the moments provided by the electrode assembly when positioned away from the center of rotation 1000 would be attenuated according to the spacing of the center electrode assembly 504 relative to the center of rotation 1000. As described above, the center of rotation 1000 is instead positioned at the center electrode assembly 504 according to the positioning of the proximal and distal support elements 404, 406 as well as their material (i.e., spring constant). The proximal and distal support elements 404, 406 thereby locate the center of rotation 1000 coincident with the center electrode assembly 504 during movement of the coupling shaft 306 and ensure the coupling shaft 306 is configured to provide maximum lateral rotation when subject to the maximum actuation voltage provided by the mechanical testing instrument 200 (see FIGS. 2A, 2B).

The nanomechanical test system 100 shown in FIG. 1 includes electronic components with the mechanical testing instrument 102 (e.g., an electromechanical transducer) configured for generation of actuation voltages and measurement of displacement and forces. As previously described, the electronics of the nanomechanical test system 100 provide an actuation voltage that facilitates the actuation of the probe tip, such as the probe tip 304 shown in FIG. 3 in one or more of the normal and lateral directions. Movement of the probe tip 304 where the probe tip is coupled with the capacitor assembly 402 shown in FIGS. 4A and 4B generates a displacement signal 152 as shown in FIG. 1. The displacement signal 152 is interpreted by the electronics of the nanomechanical test system 100 to determine the displacement of the probe tip 304 during use of the mechanical testing instrument 102. Optionally, where a second actuator is used to move the probe tip 104, for instance a piezo actuator (e.g., a 3D coarse positioner 112 or 3D fine positioner 114 shown in FIG. 1), the actuation voltage 150 shown in FIG. 1 is a static null voltage applied to the actuator 106 to maintain the probe tip 304 static relative to the remainder of the transducer assembly 400 (see FIGS. 4A, 4B). The null static voltage used to hold the probe tip 304 static is interpreted in a similar manner as the displacement signal 152 shown in FIG. 1 by the electronics of the nanomechanical test system 100 and when interpreted provides the incident forces on the probe tip 304, for instance one or more of the normal and lateral forces incident on the probe tip 304.

Figure 11:
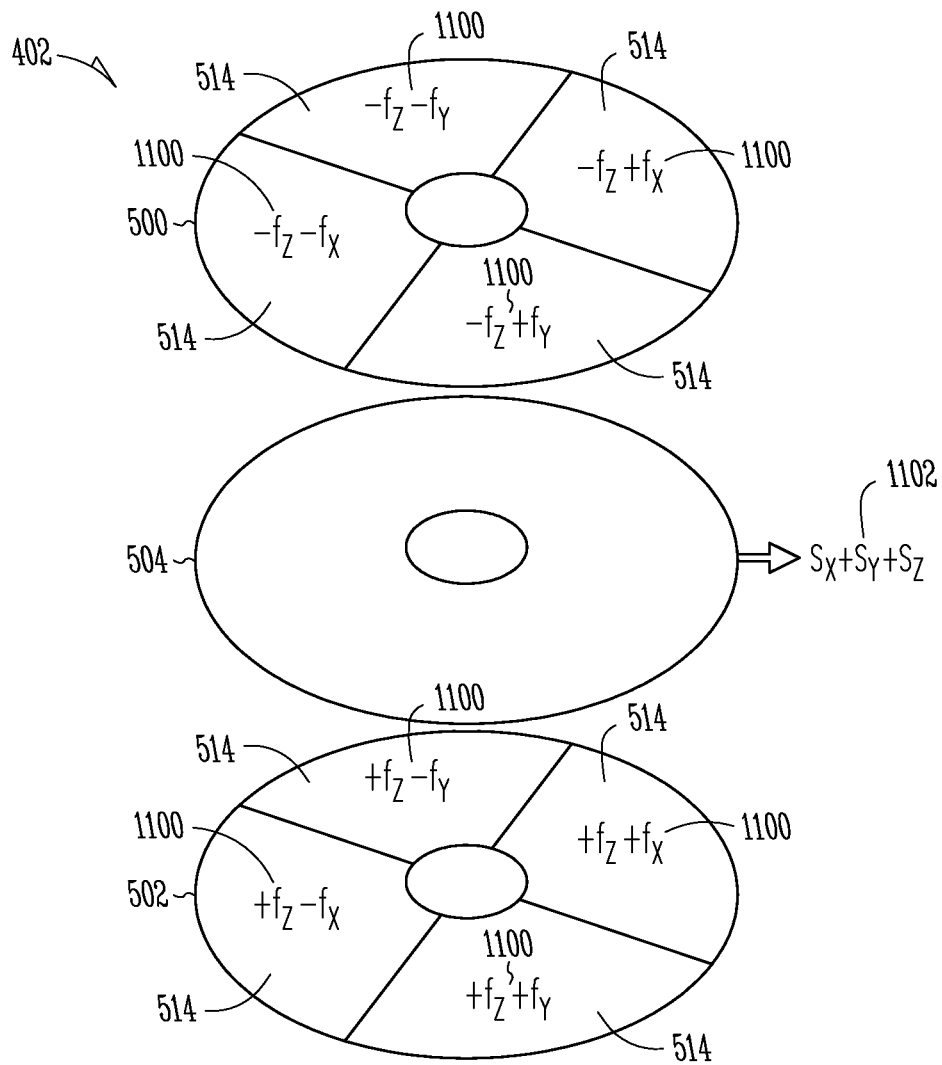
FIG. 11 is a schematic exploded view of the multi-zoned capacitor with individual excitation input signals and a composite output signal.

Referring now to FIG. 11, one schematic example of the capacitor assembly 402 is shown with excitation signals provided to the first and second counter electrodes 500, 502 as well as a composite output signal provided at the center electrode assembly 504. As previously described in one example, the capacitor assembly 402 includes first and second counter electrodes 500, 502 with a center electrode assembly 504 interposed therebetween. The first and second counter electrodes 500, 502 are each divided into two or more sections such as the electrode quadrants 514 shown in FIG. 11 (see also FIGS. 5A, 5B). As shown in FIG. 11, each of the sections 514 of the first and second counter electrodes 500, 502 receives a sectional excitation signal 1100. Each of the sectional excitation signals 1100 is different relative to the excitation signals incident on the other electrode sections 514. Application of the sectional excitation signals 1100 in one example is used to actuate the center electrode assembly 504. As previously described, actuation of the center electrode assembly 504 provides one or more of normal and lateral movement of the probe tip 304 shown in FIG. 3. In another example, the sectional excitation signal 1100 includes static null signals transmitted through the first and second counter electrodes 500, 502 to hold the assembly of the center electrode assembly 504, the coupling shaft 306 and the probe tip 304 static relative to the remainder of the transducer assembly 400. The application of the sectional excitation signals 1100 results in a composite output signal 1102 having corresponding axial components according to the sectional excitation signals 1100.

As will be described in further detail below, the sectional excitation signals 1100 are generated according to component excitation signals corresponding to one or more axes, including for instance the X, Y and Z axes. As the sectional excitation signals 1100 are provided to the first and second counter electrodes 500, 502, the resulting composite output signal 1102 includes measurable electrical characteristics that when properly interpreted show one or more of the displacement of the center electrode assembly 504 (one or more of normally and lateral displacement) as well as the forces incident on the probe tip 304. As will be described in further detail below, the sectional excitation signals 1100 are generated with a modulator, and the resulting composite output signal 1102 is demodulated with a demodulator. The modulator and demodulator cooperate to provide measurable excitation signals to the capacitor assembly 402 and interpretation of the resulting composite output signal 1102 to determine one or more of displacement of the center electrode assembly 504 as well as the forces incident on the probe tip 304 coupled with the center electrode assembly 504. Optionally, the modulator provides sectional excitation signals 1100 including static null signals configured to constrain the center electrode assembly 504 to a static orientation relative to the remainder of the transducer assembly 400. The resulting composite output signal 1102 is interpreted by the demodulator to measure the resulting forces and moments incident on the center electrode assembly 504, for instance, through the engagement of the probe tip 304 with the sample. Optionally, the transducer assembly 400 is configured for passive operation. The transducer assembly 400 receives no actuation signals or static null signals. Instead, excitation signals are provided to facilitate measurement of one or more of the displacement of the probe tip 304 or forces incident on the tip. Sectional excitation signals 1100 provide one or more input signals to the capacitor assembly 402, and the composite output signal 1102 corresponds to displacement of the center electrode assembly 504 as the probe tip is moved (e.g., through piezo actuation) relative to the sample in one or more of lateral and normal directions.

Figure 12:
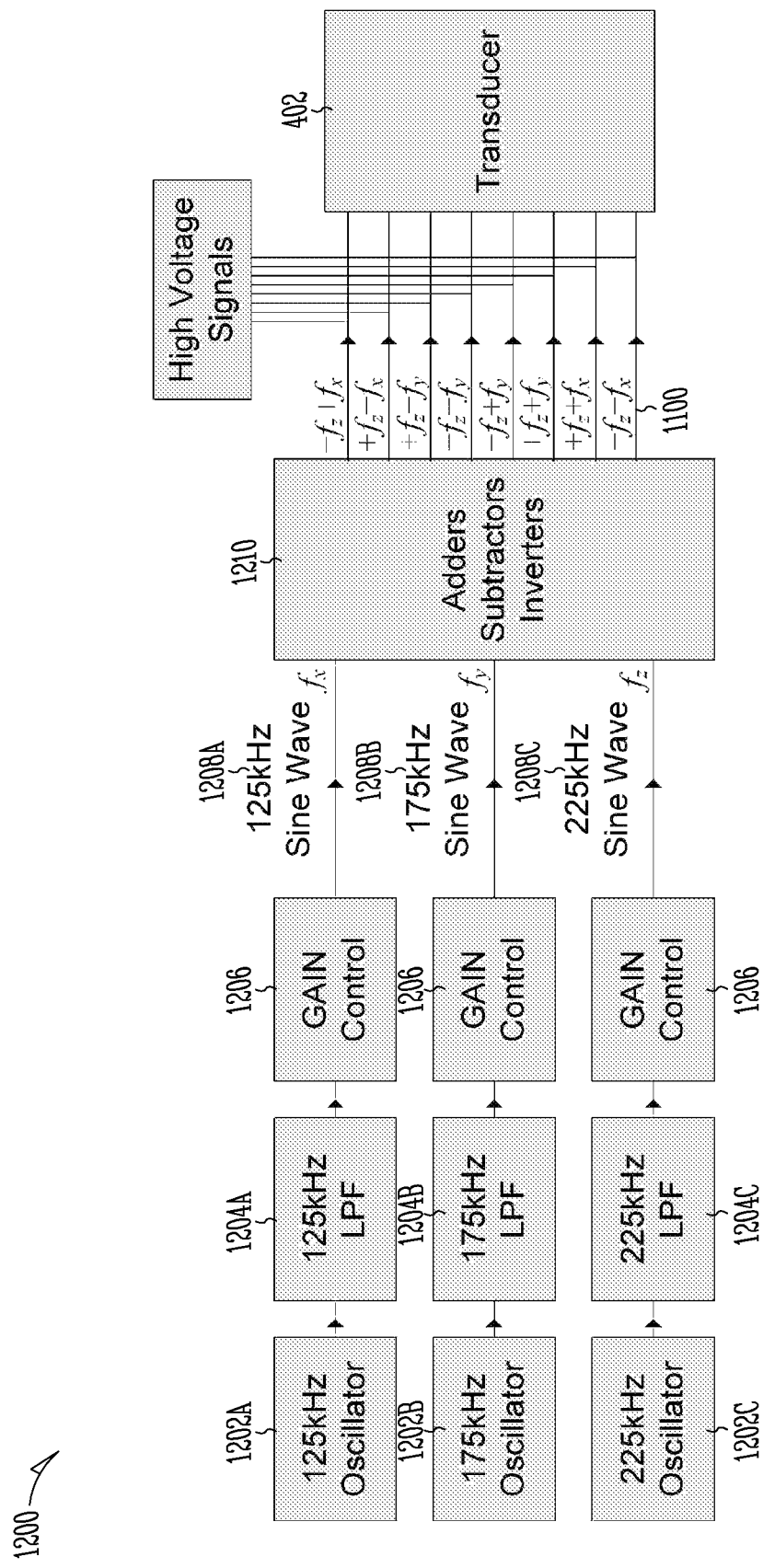
FIG. 12 is a block diagram showing one example of a modulation system for transmitting multiple individual excitation input signals to the three-dimensional supported transducer shown in FIG. 4.

FIG. 12 shows one example of a modulator 1200. The modulator 1200 is optionally included in the controller 116 shown in FIG. 1. In the case of the transducer assembly 400 shown in FIGS. 4A and 4B configured for 3D actuation as well as displacement and force measurement, the modulator 1200 includes a plurality of oscillators 1202A-C configured to generate square waves according to each of the axes the transducer assembly 400 is configured to actuate or measure (e.g., the x, y and z axes). The signals generated by the oscillators 1202A-C are sent through low-pass filters 1204A-C for conditioning of the signals into sinusoidal waves of desired frequency and amplitude. In the example shown in FIG. 12, the sinusoidal waves generated by the oscillators 1202 A-C and the low-pass filters 1204 A-C have individual frequencies of 125 kilohertz for the X component signal, 175 kilohertz for the Y component signal, and 225 kilohertz for the Z component signal. As shown, the signals are sent through gain controls 1206 which result in the component excitation signals 1208A-C corresponding to the axes of actuation and measurement of the transducer assembly 400 (e.g., X, Y, and Z axes). The component excitation signals 1208A-C are then sent through an adder/subtractor/inverter module 1210 to generate the sectional excitation signals 1100 for transmission to the first and second counter electrodes 500, 502 of the capacitor assembly 402. As described previously, the sectional excitation signals 1100 are generated according to the component excitation signals 1208A-C. Stated another way, each of the sectional excitation signals 1100 contain signal components for one or more of the axes of actuation and measurement used in the transducer assembly 400.

Referring again to FIG. 11, as shown the sectional excitation signals 1100 are transmitted to the first and second counter electrodes 500, 502. Transmission of the sectional excitation signals 1100 in one example actuates the center electrode assembly 504 and generates a composite output signal 1102. The composite output signal includes measurable electrical characteristics based on the sectional excitation signals 1100 as well as one or more of lateral displacement of the probe tip, normal displacement of the probe tip, forces incident on the probe tip whether lateral, normal or both, torques and the like.

Figure 13:
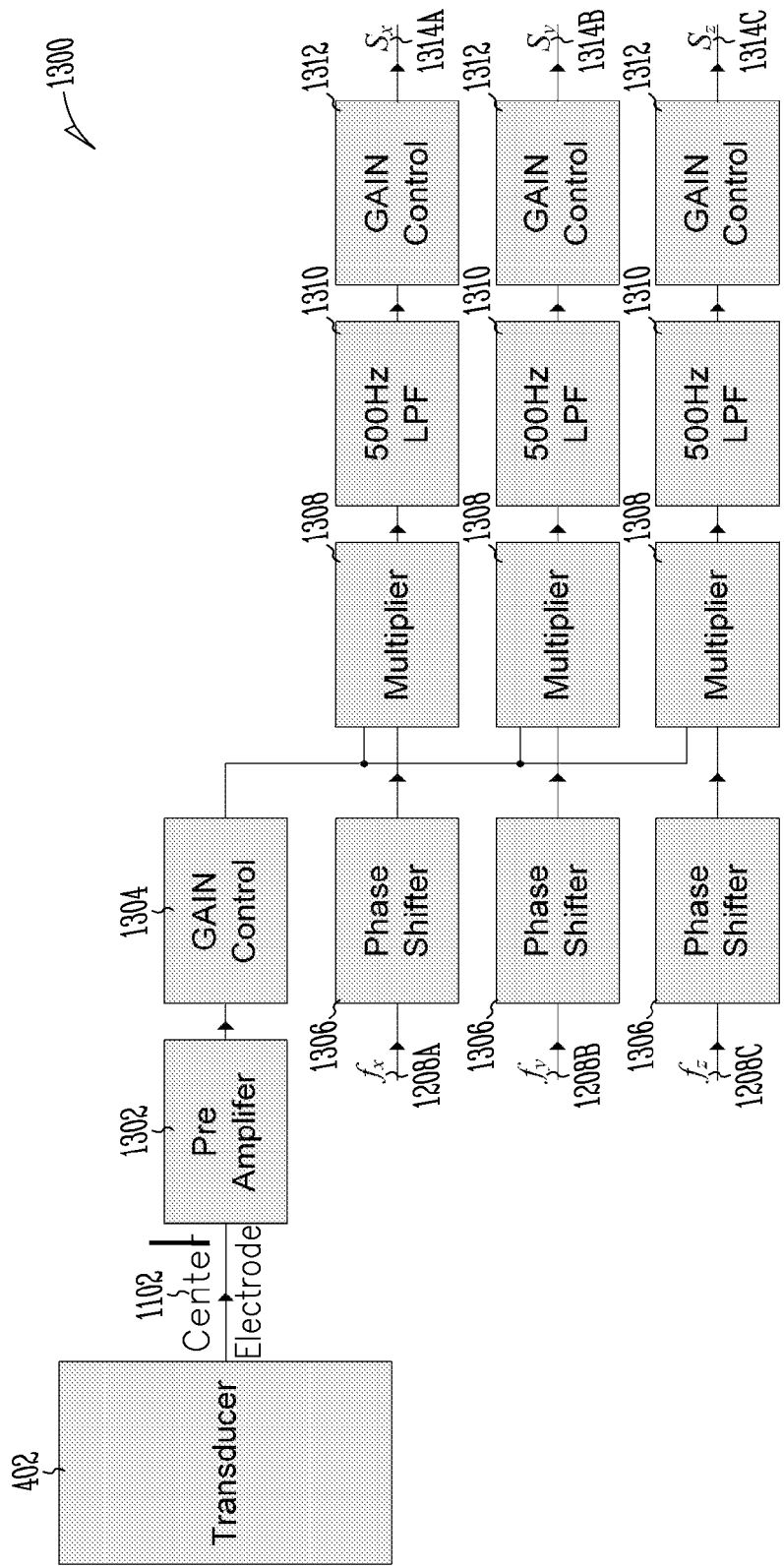
FIG. 13 is a block diagram showing one example of a demodulation system for receiving and demodulating the composite output signal from the three-dimensional supported transducer shown in FIG. 4.

Referring now to FIG. 13, one example of a demodulator 1300, for instance contained within the controller 116 shown in FIG. 1, is provided. As previously described, a composite output signal 1102 is provided by the center electrode assembly 504 of the capacitor assembly 402. The composite output signal 1102 is transmitted through a preamplifier 1302 and gain control 1304 before being interpreted and discriminated by a plurality of multipliers such as multipliers 1308.

After amplification, the composite output signal 1102 is transmitted to multiplier 1308 within the demodulator 1300. The component excitation signals 1208A-C from the modulator 1200 are transmitted to phase shifters 1306 within the demodulator 1300. The phase shifters 1306 phase shift the component excitation signals 1208A-C to correct for phase shifting caused by wire length, capacitance and the like to bring the component excitation signals 1208A-C into phase with the composite output signal 1102. The component excitation signals 1208A-C (e.g., phase shifted component reference signals) are then submitted to each of the multipliers 1308 and multiplied with the composite output signal 1102. Multiplication of the composite output signal 1102 yields individual signals corresponding to each of the axes of the relative component excitation signals 1208A-C. In other words, multiplication by the component excitation signals 1208A-C increases the amplitude of the composite signal for the various axes and highlights the desired axial components. For instance, the composite output signal 1102 is multiplied by the X axis component excitation signal 1208A to generate a component output signal 1314A corresponding to the X axis that includes one or more of displacement and force measurements along the X axis. After multiplication, the resulting signals are then passed through low-pass filters 1310 to remove AC components from the signals and provide only DC components at the gain controls 1312. The resulting component output signals 1314A-C provide displacement and force measurements for each of the axes of the transducer assembly 400.

Figure 14:
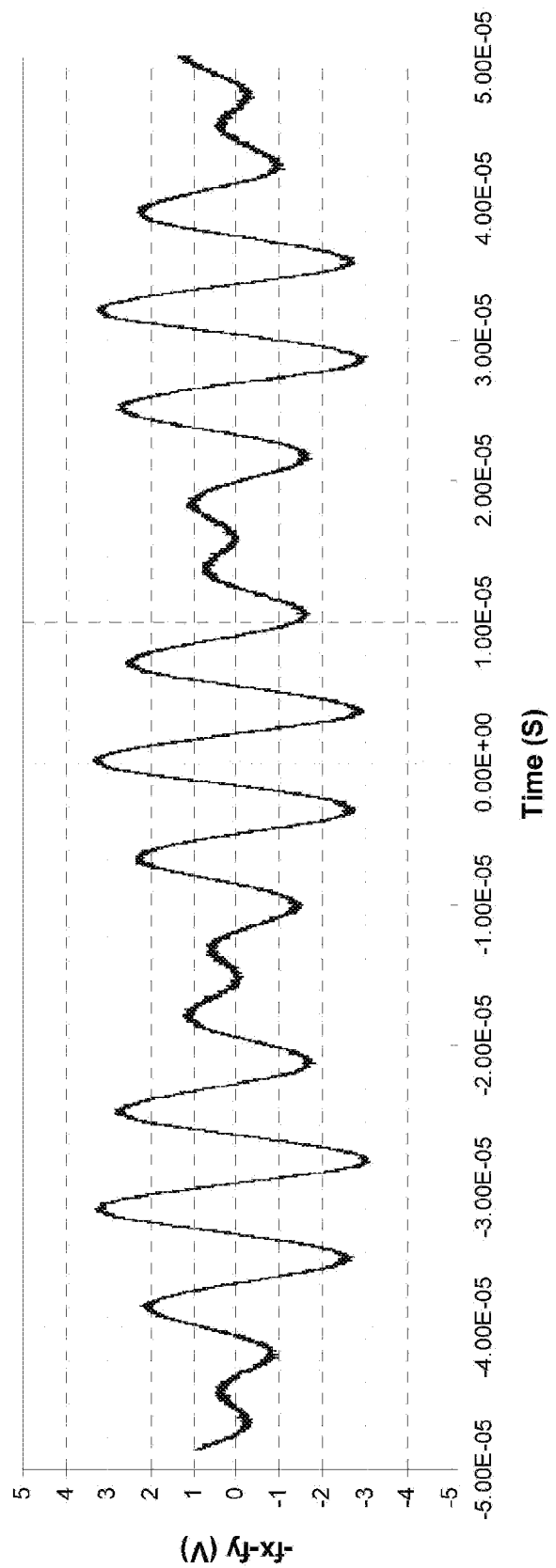
FIG. 14 is one example of an individual excitation input signal input to one zone of the multi-zoned capacitor used in the three-dimensional transducer.

Referring to FIG. 14, one example of a sectional excitation signal 1100 is provided. In the example shown in FIG. 14, the sectional excitation signal corresponds to one of the excitation signals provided to a single section of one of the first and second counter electrodes 500, 502. As shown in FIG. 14, the sectional excitation signal 1100 includes a variety of sinusoidal waves thereby providing the resulting wave function shown. The sectional excitation signal shown in FIG. 14 is generated, for instance, with the modulator 1200 shown in FIG. 12. The sectional excitation signal 1100 forms one of the excitation signals transmitted to the first and second counter electrodes 500, 502. The composite output signal 1102 as previously described is generated according to the sectional excitation signals 1100 such as the one shown in FIG. 14. Demodulation of the composite output signal 1102 with the demodulator 1300 uses the sectional excitation signals 1100 as well as displacement and force measurements (for instance, through voltage and capacitance changes and other electrical characteristics) and generates the component output signals 1314A-C shown in FIG. 13.

In one prophetic example, when the reference signal and the amplified sensor signal are in phase the output of the multiplication is:

$$\frac{V_r V_s (\sin^2 \omega t)}{10V} = \frac{V_r V_s}{20V}(1 - \cos 2\omega t)$$

The first term on the equation, $$\frac{V_r V_s}{20V},$$

is the DC part, and the second term, $$\frac{V_r V_s}{20V}(\cos 2\omega t),$$

is the AC part (at twice the input frequency), which can be filtered using the low pass filter 1310. $V_r$ is the reference signal and $V_s$ is the sensor signal. The filtered signals are further amplified and the gain of the amplifier adjusted through a potentiometer to match the signal output range to the full range of the data acquisition ADC 138 (as shown in FIG. 1). The full voltage output of the preamplifier 1302 for each channel is limited to +−10V. The overall transfer function for the electronics is:

$$V_{out} = V_r V_{in} \frac{1}{20} \frac{C_s}{C_f} A_p A_f$$

Where $V_r$ is the reference voltage amplitude and $V_{in}$ is the excitation amplitude, $A_p$ is the gain before multiplier 1308 and $A_f$ is the output gain (e.g., through gain control 1312) after low pass filtering. At unity gain this circuit will yield 0.9375 mV for 1.5 fF change in capacitance. The capacitance change per micrometer for lateral displacement for a two segment pair is around about 1.5 fF. An overall 10× gain will yield 9.375 mV per micrometer for lateral displacement sensing and 175 mV/micrometer for normal displacement sensing (28 fF/micrometer for 4 segments in normal direction). This sensitivity is adequate for nanotribology testing applications and a significant improvement over previous designs and can be measured directly by a 24 bit ADC 124 data acquisition and control system, such as DSP128 shown in FIG. 1.

As previously described the mechanical testing instrument 200 and the electronics described herein are configured for one or more of actuation and measurement of displacement and forces in three dimensions. A variety of exemplary control schemes are discussed below. Additionally, a control scheme table is included with a plurality of variables that are selected according to the needs of a specific mechanical test program. The nanomechanical test system 100 is configured for a mechanical test program by selecting and setting one or more of the plurality of variables as needed. The control scheme table provided herein includes at least four features used for the development of control schemes for use with the mechanical testing instrument, such as the mechanical testing instrument 200 and the nanomechanical test system 100 shown in FIGS. 1 and 2A and 2B.

| Control Scheme Table | | | |
|---|---|---|---|
| Actuator | Piezo Actuator | Transducer Assembly 400 | |
| Variable Controlled | Load | Displacement | |
| Control Algorithm | Closed Loop | Open Loop | |
| Axis (Axes) Controlled | X | Y | Z | Combination |

As shown in the control scheme table, these four features include, but are not limited to, the actuator type, the variable controlled, a control algorithm, and the axis or axes controlled by the control scheme. As shown in the control scheme table, the nanomechanical test system 100 including the mechanical testing instrument 200 having a transducer assembly 400 (which includes the capacitor assembly 402) may be used in a variety of configurations with differing variables controlled and control algorithms with any combination of axes (or axis) controlled through the control algorithm.

Referring first to the actuator feature shown in the table, the actuator used in the control scheme to move the probe tip 304 coupled with the coupling shaft 306 includes a piezo actuator such as the 3D coarse positioner 112 and the 3D fine positioner 114 shown in FIG. 1. In such a configuration, the piezo actuators move the transducer assembly 400 including for instance the transducer assembly 400 (e.g., a capacitor assembly 402 with the proximal and distal support springs 404, 406, and the like) and the transducer body 308. In another example, the actuator includes the transducer assembly 400. As previously described, the transducer assembly 400 includes the capacitor assembly 402 having the first and second counter electrodes 500, 502 as well as the center electrode assembly 504. Either of the piezo actuator or transducer assembly 400 is configured for applying loads and displacements to a sample while the probe tip 304 is engaged with the sample.

Referring again to the control scheme table, the second feature described includes the variable controlled, for instance during actuation of one of the piezo actuator and the transducer assembly 400. As shown in the control scheme table, the variables controlled in one or more of the control schemes include load and displacement. With load control the force or torque applied to the sample with the probe tip 304 is controlled with the control scheme. In displacement control the displacement of the probe tip 304 relative to the sample in one or more of lateral and normal directions is controlled. Control schemes using these controlled variables further include control algorithms such as closed-loop and open-loop algorithms to apply load and displacement according to specified force or displacement functions. For instance, where a closed-loop control algorithm is used, the transducer assembly 400 measures one or more of load and displacement of the probe tip 304 relative to the sample and adjusts the actuation voltage to the piezo actuator or transducer assembly 400 to ensure the probe tip 304 loads or displaces over the sample (or both) according to a set scheme (for instance, such as gradual loading and unloading over time and gradual displacement over time).

With an open-loop configuration, one or more of the piezo actuator and the transducer assembly 400 does one or more of moving the probe tip 304 and engaging the probe tip 304 with the sample according to a set load or displacement function. For instance, with an open-loop control algorithm, the piezo actuator or transducer assembly 400 receives actuation voltages according to a set function configured to apply a specified load according to the specified voltage or a specified displacement according to the specified voltage without any feedback adjustments for the actual movement or loading of the probe tip 304.

Referring again to the control scheme table, the control schemes are configured for controlling movement or loading of the probe tip 304 in one or more axes such as the X, Y, and Z axes or any combination thereof. For instance, in one example with a closed-loop control algorithm for the X and Y axes, the probe tip 304 is scribed over a sample and the feedback of the control algorithm ensures the probe tip 304 scribes across the sample in a specified time and over a specified distance. In such a control scheme, the Z axis, for example, may be left uncontrolled and one or more of displacement and load measurements are made normally with respect to the probe tip 304 along the Z axis.

Although one example is described with this control scheme, any number of combinations of actuators, variables controlled, control algorithms, and axes are considered within the bounds of the features described in the control scheme table, and the nanomechanical test system 100 described herein is configured to operate according to any of the various permutations. Stated another way, the transducer assembly 400 configured for actuation and measurement in the lateral and normal directions is configured for the measurement of loads and displacement of the probe tip 304 during any control scheme.

As previously described and shown, for instance in FIGS. 5A and 5B, the transducer assembly 400 includes a capacitor assembly 402 having first and second counter electrodes 500, 502 with a plurality of sections on each of the counter electrodes. The plurality of sections 514 facilitate the actuation and measurement of forces and displacement along each of the lateral axes (X and Y) and the normal axis (Z axis). As shown, for instance, in FIG. 11, the first and second counter electrodes 500, 502 receive sectional excitation signals 1100 and the center electrode assembly 504 generates a composite output signal 1102 based in part on the sectional excitation signals 1100 (e.g., actuation voltages and static null voltages). The composite output signal 1102 further includes components corresponding to displacement and force incident on the probe tip 304 coupled with the center electrode assembly 504 through the coupling shaft 306. That is to say, in whatever control scheme the nanomechanical test system 100 is configured, the transducer assembly 400 is configured for measurement of loads and displacement on the probe tip 304 in one or more of the X, Y, and Z axes or any combination thereof.

Several exemplary control schemes are provided below. The exemplary control schemes are not intended to be limiting but instead provide examples of control schemes within the broad umbrella provided with the control scheme table provided herein and previously described.

One example of a control scheme includes a closed-loop displacement control scheme. In this exemplary control scheme, the piezo actuator (one or more of the 3D coarse positioner 112 and the 3D fine positioner 114) are held static while the transducer assembly 400 (configured for movement and measurement of force and movement in the X, Y, and Z axes) scratches or indents (displaces) according to a set function. The transducer assembly 400 including the capacitor assembly 402 is used to measure the load during to displacement. The actuation force in this control scheme is provided by the transducer assembly 400 including the capacitor assembly 402 having the first and second counter electrodes 500, 502 and the center electrode assembly 504 as previously described herein. The actuation force provided by the transducer assembly 400 includes one or more of indentation or lateral movement of the probe tip 304 such as scratching across a sample. In this control scheme, the displacement of the probe tip 304 is controlled (in contrast to load control). A closed-loop (feedback) algorithm is used to control the displacement of the probe tip 304 and ensure the probe tip 304 displacement follows a predetermined displacement versus time function. While the transducer assembly 400 is applying the actuation voltage resulting in the displacement according to the displacement versus time function of the control algorithm, the composite output signal 1102 from the center electrode assembly 504 (see FIG. 11) includes measurable electrical characteristics such as voltage or capacitance that allow for the measurement of the displacement of the probe tip 304 as well as the force and moment incident on the probe tip 304. The transducer assembly 400 thereby provides the actuation forces needed for displacing the probe tip 304 according to the displacement versus time function (controlled with a feedback or closed-loop control algorithm) and the transducer assembly 400 is further configured to simultaneously measure one or more of the force incident on the probe tip 304 as well as the displacement of the probe tip 304 relative to the sample.

Another example of a control scheme includes a closed-loop null tip position control scheme. In this scheme the piezo actuator, such as the fine and coarse actuators 112, 114 shown in FIG. 1, provide indentation or scratching of the probe tip 304 while the probe tip 304 is held static (e.g., null) with respect to the remainder of the transducer assembly 400. Stated another way, the piezo actuator moves the entire transducer assembly 400 including the transducer body 308, the capacitor assembly 402, the coupling shaft 306, and the probe tip 304 while the probe tip 304 is otherwise held static relative to the capacitor assembly 402. The transducer assembly 400 including the capacitor assembly 402 instead applies counter voltages that apply counter forces and moments at the center electrode assembly 504 to maintain the coupling shaft 306 and the probe tip 304 static relative to the remainder of the transducer assembly 400. For this control scheme, the counter forces and moments applied to maintain null tip position are equivalent to the sample forces generated through engagement between the probe tip 304 and the sample. With the closed-loop null tip position control scheme, the actuation force is provided by the piezo actuator such as the fine and coarse actuators 112, 114 as previously described. In one example, the piezo actuator is actuated to provide displacement according to an open-loop control scheme causing specified displacement over a period of time. In another example, the transducer assembly 400 including the capacitor assembly 402 applies a specified Z-axis force while the Z-axis piezo actuator is closed loop controlled to maintain the probe tip 304 at the null position (with respect to the normal Z axis). In this mode of operation, the piezo actuator moves the whole transducer assembly along the X and Y axes and the capacitor assembly 402 generates counter forces to maintain the probe tip 304 at a null position relative to the transducer body 400 and the X and Y axes. In this operation, the sample force incident on the probe tip 304 is the combination of the specified Z-axis force and the counter X and Y component forces all generated by the capacitor assembly 402.

In another example, the piezo actuator is held static while the transducer assembly 400 is actuated to scratch (laterally move) or indent the probe tip 304 according to a set load control function. The transducer assembly 400 including the capacitor assembly 402 is further used to measure the displacement of the probe tip 304 as it moves relative to the sample. In this open-loop type of control scheme, the actuation force is provided by the transducer assembly 400, for instance, the first and second counter electrodes 500, 502 and the center electrode assembly 504 of the capacitor assembly 402. Actuation voltages are changed according to the set function (e.g., relative to time) to actuate the probe tip 304. The open-loop control algorithm used with the open-loop control scheme approximates a load control type algorithm (e.g., a feedback or closed-loop algorithm and other control schemes). As the actuation voltage is applied, the composite output signal 1102 (see FIG. 11) from the center electrode assembly 504 is measured to determine the load and displacement incident on the probe tip 304. For instance, one or more of a change in voltage or change in capacitance at the capacitor assembly 402 is used to measure one or more of the load or displacement of the probe tip 304 during actuation by the transducer assembly 400. In the open-loop control scheme then, the transducer assembly 400 provides the actuation for the probe tip 304 while at the same time also measuring the displacement and load incident on the probe tip 304.

In still another example, a control scheme includes a completely passive configuration where the transducer assembly 400 is used solely to measure one or more of load and displacement incident on the probe tip 304 without providing any actuation to the probe tip 304. Instead, the piezo actuator is operated in one or more axes to move the probe tip 304 relative to a sample, for instance, to indent the probe tip, move it laterally, a combination of both, and the like. In one example testing scenario including this configuration, the piezo actuator such as one or more of the fine and coarse positioners 112, 114 shown in FIG. 1 laterally move (scratch) the probe tip 304 while the displacement of the probe tip 304 along the Z axis (normal) is controlled by a closed-loop algorithm to ensure the application of a predefined normal force on the sample. In this configuration, the X and Y axes (lateral movement) are open-loop controlled according to a predefined displacement versus time function. The transducer assembly 400 as previously described does not actuate the probe tip 304 but senses displacement along the X, Y, and Z axes. The sample force is thereby estimated based on the displacement of the probe tip 304 along these axes. For instance, as shown at FIG. 11, the composite output signal 1102 includes electrical characteristics corresponding to the displacement of the center electrode assembly 504 relative to the first and second counter electrodes 500, 502. Further, in this particular configuration, closed-loop control using the transducer assembly 400 having the capacitor assembly 402 therein is used to generate a feedback signal to control the actuation of the piezo actuator along the Z axis. By controlling the displacement of the probe tip 304 along the Z axis, the piezo actuator is configured to correspondingly apply a predefined normal force on the sample. The predefined normal force applied to the probe tip 304 through the transducer assembly 400 results in displacement of the probe tip 304 as the probe tip is moved across the sample. The transducer assembly 400 uses the composite output signal 1102 to measure the displacement of the probe tip 304 along the Z axis.

In yet another example, with a similar control scheme to the passive configuration described immediately above, the Z axis (in a similar manner to the X and Y axes) is open-loop controlled through the piezo actuator. Stated another way, the piezo actuator moves the probe tip 304 according to a set displacement versus time function or force versus time function with no feedback control through transducer assembly 400 sensing. In this particular control scheme, the transducer assembly 400 applies no actuation to the coupling shaft 306 and the probe tip 304 coupled thereto. Instead, the transducer assembly 400 is entirely passive and measures one or more of displacement and load in one or more of the X, Y, and Z axes.

Figure 15:
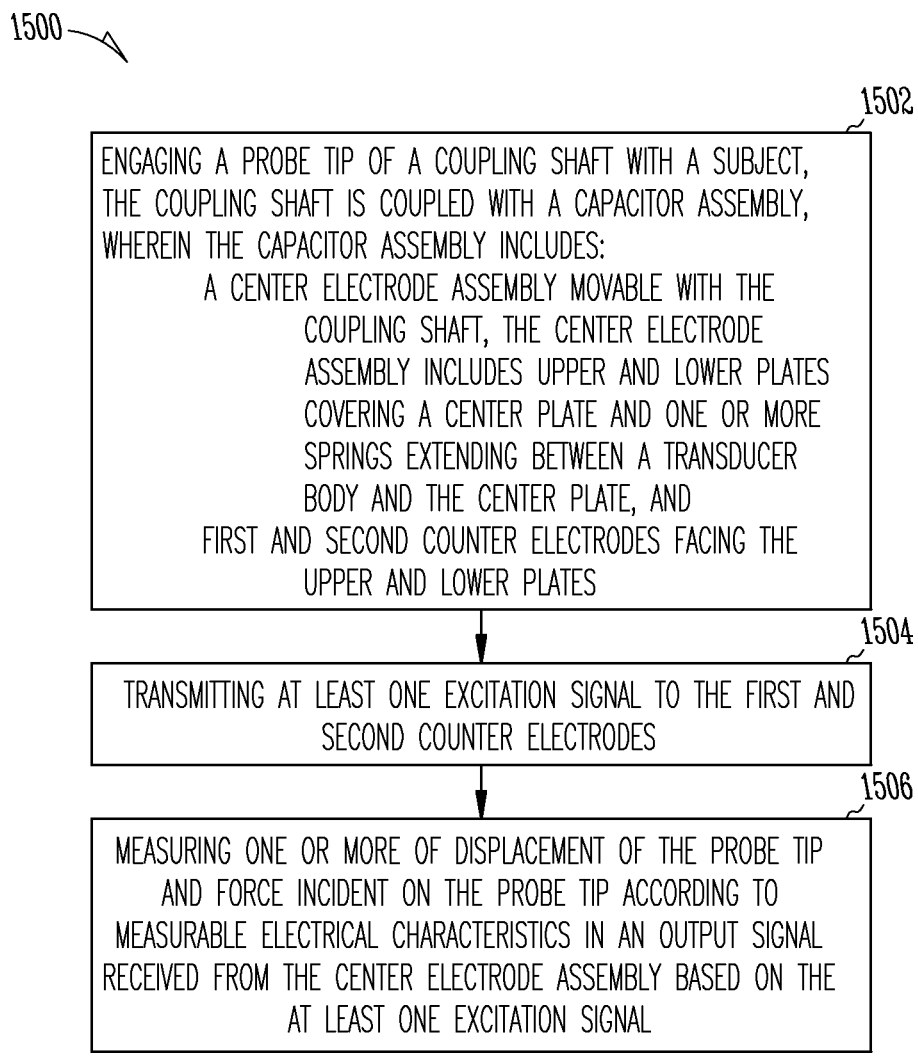
FIG. 15 is a block diagram showing one example of a method for using a testing instrument configured for three dimensional movement or measurement.

FIG. 15 shows one example of a method 1500 for using a testing instrument configured for three dimensional movement or measurement at one or more of a nano or micron scale. The method 1500 is conducted with mechanical testing assembly 200 including the mechanical testing instrument 300 previously shown in FIGS. 2A, B and 3. In describing the method 1500 reference is made to features and elements previously described herein including numbered references where convenient. Numbered elements provided within the description of the method 1500 are not intended to be limiting. Instead, numbered references are provided for convenience and further include any similar features described herein as well as their equivalents. At 1502, the method 1500 includes engaging a probe tip, such as the tip 304 shown in FIG. 3, of a coupling shaft 306 with a subject. The coupling shaft 306 is coupled with a capacitor assembly 402 wherein the capacitor assembly 402 includes a center electrode assembly 504 movable with the coupling shaft 306. The center electrode assembly 504 includes upper and lower plates 510, 512 covering both a center plate 600 and one or more springs 606 extending from the center plate 600, for instance, toward the transducer body 308. In one example, the one or more springs 606 are coupled between the transducer body 308 and the center plate 600, for instance, with a center electrode ring 509, as shown in FIG. 6. The capacitor assembly 402 further includes first and second counter electrodes 500, 502 oriented toward each of the respective upper and lower plates 510, 512. As described herein, in one example, the upper and lower plates 510, 512 and the first and second counter electrodes 500, 502 are maximized with respect to area (e.g., within the footprint or volume available in the transducer body 308) to thereby correspondingly optimize the overlapping area between the first and second counter electrodes and the opposed upper and lower plates.

At 1504, at least one excitation signal is transmitted to the first and second counter electrodes 500, 502. In one example, the at least one excitation signal includes, but is not limited to, a plurality of component excitation signals, such as the signals 1208A-C shown in FIG. 12. In such an example, the plurality of component excitation signals include component signals intended to measure force and displacement of the center electrode assembly 504 in one or more of normal and lateral directions.

At 1506, the method 1500 includes measuring one or more of the displacement of the probe tip 304 and forces incident on the probe tip according to measureable electrical characteristics (e.g., capacitance, voltage and the like) in an output signal received from the center electrode assembly 504 based on the at least one excitation signal. In one example, the output signal received from the center electrode assembly 504 includes a composite output signal 1102 as previously shown in FIG. 11. In another example, the composite output signal 1102 is in one example split into component output signals 1314A-C to measure one or more of normal and lateral displacement and forces incident on the probe tip 304 (including displacement and force applied to the probe tip by the capacitor assembly 402), as described herein. That is to say, the methods and systems described herein allow for three dimensional actuation and measurement of displacement and forces in three dimensions.

As previously described, the overlapping area between the upper and lower plates 510, 512 and the first and second counter electrodes 500, 502 is optimized according to the configuration shown, for instance, in FIG. 6. The upper and lower plates 510, 512 at the center electrode assembly 504 cover or conceal the plate spring 606 extending between the center electrode ring 509 and the center plate 600. For instance, in one example, the plurality of plate springs 606 are received within spring recesses 608 of one or more of the upper and lower plates 510, 512 to facilitate the free movement of the plate springs 606 during movement of the center electrode assembly 504 relative to the first and second counter electrodes 500, 502. For instance, the spring recesses 608 allow the plate springs 606 therein to freely deflect during movement of the center electrode assembly 504 and thereby substantially prevent the impingement of the springs 606 against the upper and lower plates 510, 512. The free movement of the springs 606 allows the springs to support the center electrode assembly 504 during deflection but substantially prevents constraint of motion of the center electrode assembly, for instance, by the engagement of the springs 606 undesirably with another component of the center electrode assembly 504 (e.g., the upper and lower plates 510, 512).

The optimizing of the area, for instance, with the inclusion of the upper and lower plates 510, 512 overlaps the center electrode assembly 504 with the entire area of the first and second counter electrodes 500, 502 to facilitate the maximizing of forces and torque delivered through the center electrode assembly 504. Stated another way, by concealing the plurality of springs 606 of the center electrode assembly 504 the overlapping area of the center electrode assembly 504 and the first and second counter electrodes 500, 502 is maximized thereby allowing for a maximized corresponding area during force and torque generation, for instance, through excitation voltages supplied by the first and second counter electrodes 500, 502 acting upon the center electrode assembly 504. In a similar manner, the optimized overlapping area between the center electrode assembly 504 and the first and second counter electrodes 500, 502 increases the overall sensitivity of the capacitor assembly 402 as capacitance, for instance, one electrical characteristic measurable with the method 1500, is measured according to the area between the plates of the capacitor assembly 402.

Figure 16:
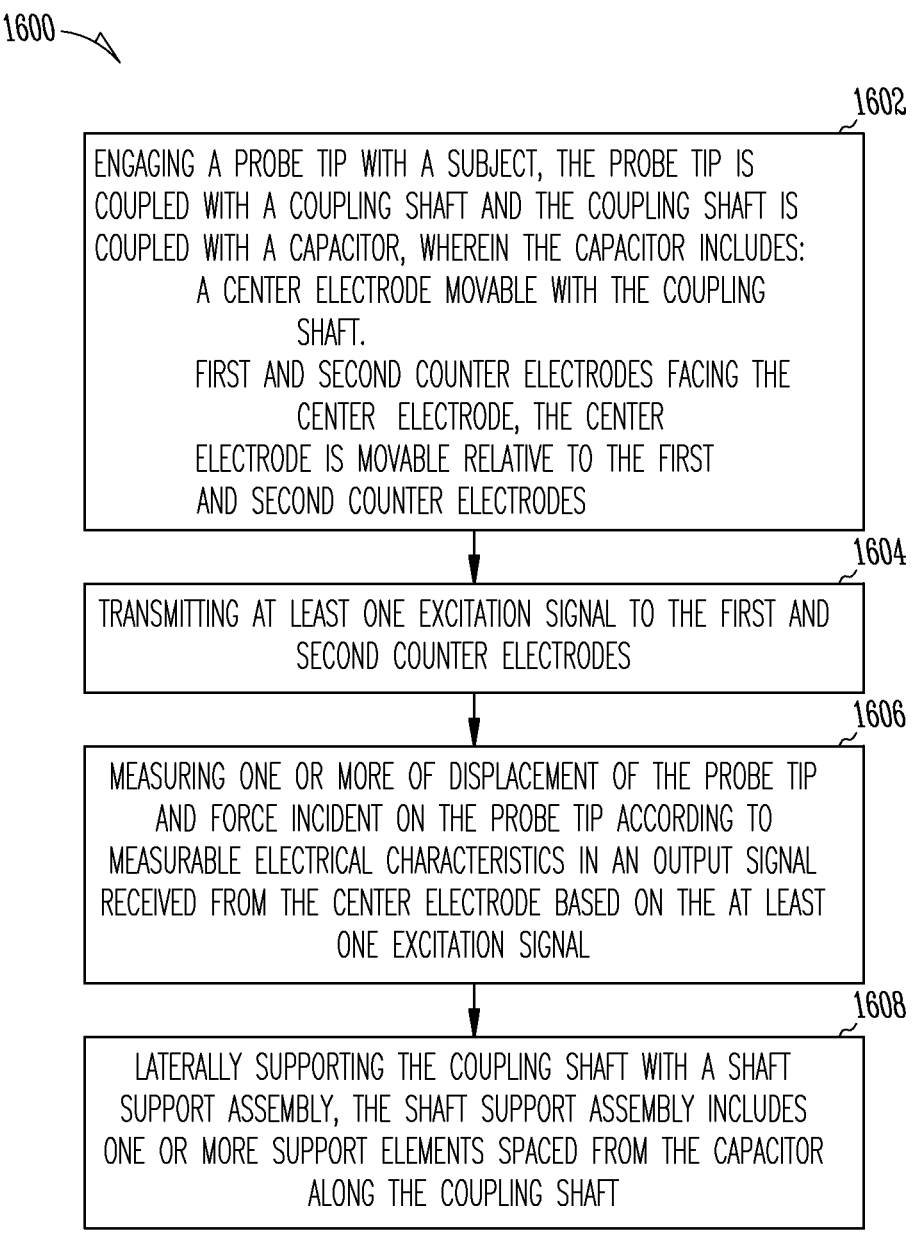
FIG. 16 is a block diagram showing another example of a method for using a testing instrument configured for three dimensional movement or measurement.

Referring now to FIG. 16, one example of a method 1600 for using a mechanical testing instrument at one or more of nano or micron scale is provided. The method 1600 is conducted with the mechanical testing assembly 300 including the mechanical testing instrument 200 previously shown in FIGS. 2A, B and 3. In describing the method 1600 reference is made to features and elements previously described herein including numbered references where convenient. The numbered elements provided within the description of the method 1600 are not intended to be limiting. Instead, numbered references are provided for convenience and further include any similar features described herein as well as their equivalents. At 1602, the method 1600 includes engaging a probe tip, such as the tip 304 with a subject. The probe tip 304 is coupled with the coupling shaft 306 as shown in FIGS. 4A, B. The coupling shaft 306 is in turn coupled with a capacitor 402. The capacitor 402, in one example, includes a center electrode 504 movable with the coupling shaft 306 and first and second counter electrodes 500, 502 facing the center electrode 504. In one example, the center electrode 504 is movable relative to the first and second counter electrodes 500, 502 as previously described herein.

At 1604, at least one excitation signal, such as the excitation signals 1208A-C, is transmitted to the first and second counter electrodes 500, 502. As previously described herein, in one example, a plurality of excitation signals 1208A-C corresponding to components of displacement or force in one or more of lateral and normal directions are supplied to the first and second counter electrodes 500, 502. At 1606, one or more of the displacement of the probe tip 304 or forces incident on the probe tip 304 (including force applied through the probe tip by the capacitor assembly 402) are measured according to measurable electrical characteristics in an output signal 1102 received from the center electrode 504 based on the at least one excitation signal. As shown, for instance in FIG. 13, in one example the composite output signal 1102 is conditioned through demodulation into the component output signals 1314A-C corresponding to one or more of measurements of forces and displacement of the center electrode 504 along a plurality of axes relative to the first and second counter electrodes 500, 502 (corresponding to movement of the probe tip 304 and forces incident on the probe tip 304). That is to say, the methods and systems described herein allow for three dimensional actuation and measurement of displacement and forces in three dimensions.

At 1608, the method 1600 further includes laterally supporting the coupling shaft 306 with a shaft support assembly 401. In one example, the shaft support assembly 401 includes one or more deflectable support elements 404, 406 spaced from the capacitor 402 along the coupling shaft 306. As shown in FIG. 4B, the proximal and distal support elements 404, 406 are positioned proximally and distally (respectively) relative to the capacitor assembly 402. As previously described herein, the provision of one or more support elements 404, 406 laterally supports the coupling shaft 306, for instance a horizontally oriented coupling shaft 306, and thereby substantially prevents the saturation of the capacitor assembly 402 sensitivity, for instance through undesirable downward rotation of an otherwise unsupported coupling shaft 306 due to gravity (but also including mechanical noise otherwise incident on the capacitor assembly 402).

As shown, for instance, in FIGS. 8 and 9, in one example, the proximal and distal support elements 404, 406 in one example include a plurality of spring elements 800 positioned in a continuous fashion around the coupling shaft 306 to provide corresponding continuous lateral support to the coupling shaft 306 at the spaced locations shown, for instance, in FIG. 8. In another example, the plurality of spring elements 800 extend in a substantially continuous fashion around the coupling shaft 306. Optionally, one or more spring channels 904 extend between each of the spring elements 800. The one or more spring channels 904 provide negligible discontinuities to the continuously extending support elements 404, 406 including the spring elements 800.

As shown, for instance in FIG. 9, the plurality of spring elements 800 extend between the coupling shaft 306 and the transducer body 308, for instance, with a plurality of spring arms 900 extending between elbows 902. The plurality of spring elbows 902 and spring arms 900 cooperate to provide robust structural support (lateral support) of the coupling shaft 306 during operation of the mechanical testing instrument 300 while at the same time allowing for deflection of the coupling shaft 306, for instance, due to the engagement of the probe tip 304 with the sample as well as actuation by way of the capacitor assembly 402. That is to say, the one or more support elements 404, 406 provide lateral support to the coupling shaft 306 but at the same time allow for deflection of the coupling shaft 306 whether laterally, normally or the like according to forces incident on the probe tip 304 and forces applied to the coupling shaft 306, for instance, by the capacitor assembly 402.

Furthermore, the shaft support assembly 401 including, for instance, one or more of support elements 404, 406 are spaced from the capacitor assembly 402 (identically or differently) to substantially ensure a center of rotation of the coupling shaft 306 is coincident with the center electrode assembly 504 of the capacitor assembly 402. Stated another way, the lateral support provided by the shaft support assembly 401 including the one or more support elements 404, 406 provides a spaced support framework to the coupling shaft 306 that moves the center of rotation of the coupling shaft 306 from an unsupported position to the supported position coincident with the center electrode assembly 504 previously shown in FIGS. 5A, B and 6. By tuning the center rotation 1000 to the position shown in FIG. 10, for instance with the one or more support elements 404, 406 spaced to provide the center of rotation 1000 at the desired position, the capacitor assembly 402 is able to maximize the forces and torques applied to the center electrode assembly 504 during operation of the mechanical testing instrument 300. That is to say attenuation of the forces and torques applied to the coupling shaft 306, for instance through undesirable positioning of the center of rotation 1000 away from the center electrode assembly 504, is substantially prevented. Instead, the center of rotation 1000 is positioned at the center electrode assembly 504 thereby optimizing the forces and torques applied to the coupling shaft 306.

FIG. 17 shows one example of a method 1700 for sensing changes in electrical characteristics in a mechanical testing instrument used in one or more of nano or micron scale mechanical testing. The method 1700 is conducted with the mechanical testing instrument 300 of the mechanical testing assembly 200 previously shown in FIGS. 2A, B and 3. In describing the method 1700, reference is made to features and elements previously described herein including numbered references where convenient. Numbered elements provided within the description of the method 1700 are not intended to be limiting. Instead, numbered references are provided for convenience and further include any similar features described herein as well as their equivalents. At 1700, a probe tip 304 is engaged with the subject. The probe tip, as previously described, is coupled with the coupling shaft and the coupling shaft 306 is in turn coupled with a capacitor assembly 402. As described herein, the capacitor assembly, in one example, includes a center electrode assembly 504 movable with the coupling shaft 306. The center electrode assembly includes upper and lower plates 510, 512 covering both a center plate 600 and one more springs 606 extending from the center plate. The capacitor assembly 402 further includes first and second counter electrodes 500, 502 facing the upper and lower plates 510, 512, respectively. Each of the first and second counter electrodes includes a plurality of sections 514 (e.g., quadrants, halves and the like) and each of the sections 514 is electrically isolated from the other sections.

At 1704, the method 1700 includes transmitting a plurality of excitation signals, such as the component excitation signals 1208A-C, to the plurality of sections 514. Each of the excitation signals associated with each section is different from the excitation signals transmitted to the other sections. As shown, for instance, in FIG. 12, in one example, the plurality of excitation signals such as component excitation signals 1208A-C are conditioned with an adder/substracter/inverter module 1210 of a modulator 1200 to generate sectional excitation signals 1100 for transmission to the first and second counter electrodes 500, 502. For instance, the sectional excitation signals 1100 shown in FIG. 12 are each supplied to one of the sections 514 shown in FIG. 5B for the first and second counter electrodes 500, 502.

At 1706, the method 1700 further includes measuring one or more of the displacement of the probe tip 304 and the forces incident on the probe tip 304 (e.g., force applied through the probe tip by the capacitor assembly 402) according to measurable electrical characteristics, such as voltage or capacitance, of the composite output signal 1102 received from the center electrode assembly 504. For instance, in one example, the component excitation signals 1208A-C are used in combination with the phase shifters 1306 (generating in phase reference signal versions of the component excitation signals 1306) of the demodulator shown in FIG. 13 to accentuate the corresponding axial components of the composite output signal 1102 and thereby generate component output signals 1314A-C as shown in FIG. 13. The mechanical testing instrument 300 is thereby able to measure the forces and displacement in normal and lateral directions for the probe tip 304 and the coupling shaft 306 coupled with the capacitor assembly 402. That is to say the mechanical testing instrument 300 is able to measure displacement of the center electrode assembly 504 and forces (and torques) transmitted to and from the center electrode assembly 504 in one or more of lateral and normal directions (i.e., in three dimensions). Stated differently, the methods and systems described herein allow for three dimensional actuation and measurement of displacement and forces in three dimensions.

CONCLUSION

The nanomechanical test system including the three-dimensional transducer assembly described herein as well as the methods for using the same provide a system with a continuous center electrode assembly and enhanced lateral stiffness through the provision of one or more support elements, such as spring support elements, coupled between the coupling shaft and the transducer body.

With the proximal and distal support elements coupled between the coupling shaft and the transducer body the lateral stiffness of the transducer assembly is enhanced. Increasing the lateral stiffness of the coupling shaft prevents saturation of the capacitor assembly and thereby ensures the capacitor assembly is sensitive to displacement of the probe tip normally and laterally. In one example, the proximal and distal support springs provide enhanced lateral stiffness that offsets displacement of the coupling shaft and the probe tip otherwise caused by gravity. Additionally, the enhanced lateral stiffness provided by the support springs minimizes undesirable displacement of the probe tip due to mechanical noise. The transducer assembly including the support springs is thereby able to reliably and accurately sense displacement and forces caused by both actuation at the capacitor assembly and movement of the probe tip.

Further, the proximal and distal support elements tune the lateral stiffness of the coupling shaft to facilitate the continued deflection of the probe tip during testing procedures while at the same time providing enhanced lateral stiffness as previously described. Stated another way, the proximal and distal support elements provide a consistent and specified spring constant that maintains support of the coupling shaft (against gravity, noise and the like) while allowing measurable displacement of the probe tip. The positioning of the support elements relative to the capacitor assembly as well as their material and configuration ensures the capacitor assembly is capable of deflection when actuated with excitation voltages or moved according to engagement and movement of the probe tip relative to a sample.

Additionally, the nanomechanical test system including the three-dimensional transducer assembly includes a continuous center electrode assembly. For instance, as previously described the center electrode assembly includes upper and lower plates overlying a center plate coupled between the coupling shaft and the transducer body with one or more plate springs. The upper and lower plates overlie the plate springs and provide a substantially continuous surface for the center electrode assembly between the coupling shaft and the inner wall of the transducer body (e.g., with a center electrode ring). The continuous surface provided by the center electrode assembly maximizes the capacitor area and allows for full utilization of the center electrode area. Because capacitance is a function of area increasing the area of the center electrode assembly correspondingly increases the sensitivity of the transducer assembly. That is to say, by increasing the area of the center electrode assembly, the assembly is able to fully overlie and underlie the first and second counter electrodes to increase the overlapping area of the capacitor assembly and correspondingly increase the capacitance of the assembly. As described herein, increasing the capacitance similarly maximizes the capacitance gradient and thereby enhances the sensitivity of the transducer assembly.

Further, by using a continuous center electrode assembly where the upper and lower plates cover the plate springs the maximum force and moment generated by the capacitor assembly is correspondingly enhanced. In the case of the maximum force generated by the capacitor assembly the increase of overlapping area provides an increase in capacitance that similarly enhances the electrostatic force that may be generated with the capacitor assembly. Further, with the increased area of the center electrode assembly and the corresponding increase in overlapping area between the center electrode assembly and the first and second counter electrodes the maximum moment generated by the capacitor assembly is also enhanced. As previously described, the area of the center electrode assembly is maximized by interposing the plate springs between the upper and lower plates of the center electrode assembly. As described herein, the increased area is provided on the peripheral portions of the center electrode assembly (e.g., near the transducer body inner wall). Similarly, the enhanced overlapping area between the center electrode assembly and the first and second counter electrodes is also provided along the peripheral area of the electrodes and the center electrode assembly. By providing additional overlapping area at peripheral portions of the center electrode assembly and the counter electrodes the capacitor assembly has a larger moment arm and thereby enhances the moment generated through actuation voltages applied to the capacitor assembly.

Various Notes and Examples

Example 1 can include subject matter (such as an apparatus, a method, a means for performing acts, or a machine readable medium including instructions that, when performed by the machine, can cause the machine to perform acts) that can include a testing instrument for mechanical testing at a one or more of nano or micron scale comprising: a transducer body; a coupling shaft; a probe tip coupled with the coupling shaft; and a capacitor housed within the transducer body, the capacitor includes: first and second counter electrodes coupled with the transducer body, and a center electrode assembly interposed between the first and second counter electrodes, the center electrode assembly is movable with the coupling shaft relative to the transducer body, and the center electrode assembly includes: a center plate coupled with the coupling shaft, one or more springs coupled between the transducer body and the center plate, an upper plate covering the center plate and the one or more springs, the upper plate is coupled with a center plate first face, and a lower plate covering the center plate and the one or more springs, the lower plate is coupled with a center plate second face.

Example 2 can include, or can optionally be combined with the subject matter of Example 1, to optionally include wherein the upper plate continuously overlies the entire first counter electrode, and the lower plate continuously overlies the entire second counter electrode.

Example 3 can include, or can optionally be combined with the subject matter of one or any combination of Examples 1 or 2 to optionally include wherein the first and second counter electrodes each include two or more to electrically isolated sections, and the upper plate continuously overlies each of the two or more sections of the first counter electrode, and the lower plate continuously overlies each of the two or more sections of the second counter electrode.

Example 4 can include, or can optionally be combined with the subject matter of one or any combination of Examples 1 or 3 to optionally include wherein the upper and lower plates extend from a coupling shaft perimeter to a position immediately adjacent to a transducer body inner perimeter, and the first and second counter electrodes extend from the coupling shaft perimeter to the position immediately adjacent to the transducer body inner perimeter.

Example 5 can include, or can optionally be combined with the subject matter of one or any combination of Examples 1-4 to optionally include wherein the first and second counter electrodes extend to first and second guard rings engaged with the transducer body inner perimeter, and the upper and lower plates extend to a center electrode ring engaged with the transducer body inner perimeter.

Example 6 can include, or can optionally be combined with the subject matter of one or any combination of Examples 1-5 to optionally include wherein one or both of the upper and lower plates include spring recesses sized and shaped to receive the one or more springs during deflection of the one or more springs.

Example 7 can include, or can optionally be combined with the subject matter of one or any combination of Examples 1-6 to optionally include wherein surfaces of the upper and lower plates facing the center plate include the spring recesses, and opposed surfaces of the upper and lower plates facing the first and second counter electrodes are continuously planar.

Example 8 can include, or can optionally be combined with the subject matter of one or any combination of Examples 1-7 to optionally include wherein each of the first and second counter electrodes include a plurality of sections and each of the plurality of sections are electrically isolated from the remainder of the other sections.

Example 9 can include, or can optionally be combined with the subject matter of one or any combination of Examples 1-8 to optionally include wherein each of the plurality of sections extend radially from a counter electrode inner perimeter adjacent to the coupling shaft to a position immediately adjacent to a transducer body inner perimeter.

Example 10 can include, or can optionally be combined with the subject matter of one or any combination of Examples 1-9 to optionally include wherein the one or more springs extend from a transducer body inner perimeter inwardly toward the coupling shaft.

Example 11 can include, or can optionally be combined with the subject matter of one or any combination of Examples 1-10 to optionally include wherein the one or more springs extend from a transducer body inner perimeter arcuately to the center plate.

Example 12 can include, or can optionally be combined with the subject matter of one or any combination of Examples 1-11 to optionally include wherein the center plate extends radially from the coupling shaft to a center plate perimeter adjacent to the transducer body inner perimeter, and the one or more springs extend through the center plate perimeter.

Example 13 can include, or can optionally be combined with the subject matter of one or any combination of Examples 1-12 to optionally include wherein the one or more springs include a plurality of spring arms and elbows positioned between each of the plurality of spring arms, and at least one of the spring arms is coupled with the center plate and another of the spring arms is coupled with the transducer body.

Example 14 can include, or can optionally be combined with the subject matter of one or any combination of Examples 1-13 to optionally include a shaft support assembly supporting the coupling shaft, the shaft support assembly includes: a deflectable proximal support element coupled between the coupling shaft and the transducer body, the proximal support element is proximally spaced from the capacitor, and a deflectable distal support element coupled between the coupling shaft and the transducer body, the distal support element is distally spaced from the capacitor and positioned between the capacitor and the probe tip.

Example 15 can include, or can optionally be combined with the subject matter of one or any combination of Examples 1-14 to optionally include wherein one or more of the proximal and distal support elements each include one or more spring elements coupled between the coupling shaft and the transducer body.

Example 16 can include, or can optionally be combined with the subject matter of one or any combination of Examples 1-15 to optionally include wherein one or more of the proximal and distal support elements continuously extend around the coupling shaft.

Example 17 can include, or can optionally be combined with the subject matter of one or any combination of Examples 1-16 to optionally include wherein the proximal and distal support elements radially engage the coupling shaft around a coupling shaft perimeter, and the proximal and distal support elements laterally support the coupling shaft against lateral movement of the coupling shaft.

Example 18 can include, or can optionally be combined with the subject matter of one or any combination of Examples 1-17 to optionally include a method. The method including a method for using a testing instrument configured for movement or measurement at one or more of a nano or micron scale comprising engaging a probe tip of a coupling shaft with a subject, the coupling shaft is coupled with a capacitor assembly, wherein the capacitor assembly includes: a center electrode assembly movable with the coupling shaft, the center electrode assembly includes upper and lower plates covering a center plate and one or more springs extending between a transducer body and the center plate, and first and second counter electrodes facing the upper and lower plates; transmitting at least one excitation signal to the first and second counter electrodes; and measuring one or more of displacement of the probe tip and force incident on the probe tip according to measurable electrical characteristics in an output signal received from the center electrode assembly based on the at least one excitation signal.

Example 19 can include, or can optionally be combined with the subject matter of one or any combination of Examples 1-18 to optionally include wherein measuring one or more of the displacement of the probe tip and force incident on the probe tip includes measuring one or more of lateral movement of the probe tip and lateral force incident on the probe tip.

Example 20 can include, or can optionally be combined with the subject matter of one or any combination of Examples 1-19 to optionally include laterally moving the probe tip across the subject with a piezo actuator coupled with a transducer body housing the capacitor assembly, and the piezo actuator moves the transducer body and the capacitor assembly with the probe tip.

Example 21 can include, or can optionally be combined with the subject matter of one or any combination of Examples 1-20 to optionally include holding the probe tip and the center electrode assembly substantially static relative to the transducer body with the at least one excitation signal transmitted to the first and second counter electrodes, wherein the at least one excitation signal includes static null position voltages.

Example 22 can include, or can optionally be combined with the subject matter of one or any combination of Examples 1-21 to optionally include wherein measuring one or more of the displacement of the probe tip and force incident on the probe tip includes measuring changes in one or more of capacitance and output voltage of the output signal.

Example 23 can include, or can optionally be combined with the subject matter of one or any combination of Examples 1-22 to optionally include wherein measuring one or more of the displacement of the probe tip and force incident on the probe tip includes measuring displacement and force in one or more dimensions including normal and lateral directions.

Example 24 can include, or can optionally be combined with the subject matter of one or any combination of Examples 1-23 to optionally include wherein transmitting at least one excitation signal includes transmitting a plurality of excitation signals to respective sections of the first and second electrodes, and measuring one or more of the displacement of the probe tip and the force incident on the probe tip includes measuring electrical characteristics of the output signal including a composite output signal based on the plurality excitation signals.

Example 25 can include, or can optionally be combined with the subject matter of one or any combination of Examples 1-24 to optionally include wherein receiving the output signal includes receiving the output signal including measurable electrical characteristics corresponding to an overlapping area of the first and second counter electrodes with the upper and lower plates, and the overlapping area extends over the one or more springs.

Example 26 can include, or can optionally be combined with the subject matter of one or any combination of Examples 1-25 to optionally include moving the center electrode assembly relative to the first and second counter electrodes in one or more dimensions including lateral and normal directions relative to the first and second counter electrodes.

Example 27 can include, or can optionally be combined with the subject matter of one or any combination of Examples 1-26 to optionally include deflecting the one or more springs extending between the transducer body and the center plate.

Example 28 can include, or can optionally be combined with the subject matter of one or any combination of Examples 1-27 to optionally include wherein deflecting the one or more springs includes deflecting the one or more springs within spring recesses in one or more of the upper and lower plates.

Example 29 can include, or can optionally be combined with the subject matter of one or any combination of Examples 1-28 to optionally include wherein deflecting the one or more springs includes maintaining separation between the one or more springs and the upper and lower plates.

Example 30 can include, or can optionally be combined with the subject matter of one or any combination of Examples 1-29 to optionally include comprising supporting the coupling shaft proximally and distally relative to the capacitor assembly.

Example 31 can include, or can optionally be combined with the subject matter of one or any combination of Examples 1-30 to optionally include wherein supporting the coupling shaft proximally and distally includes transmitting static null moments to the coupling shaft from proximal and distal support springs, the proximal and distal support springs maintaining the probe tip substantially horizontal relative to an unsupported static position.

Example 32 can include, or can optionally be combined with the subject matter of one or any combination of Examples 1-31 to optionally include generating one or more values based on the measured displacement of the probe tip and force incident on the probe tip, the one or more values consisting of at least one of elastic modulus, hardness, coefficient of friction, normal stiffness, and lateral stiffness.

Example 33 can include, or can optionally be combined with the subject matter of one or any combination of Examples 1-32 to optionally include a testing instrument for mechanical testing at one or more of nano or micron scale. The testing instrument including: a transducer body; a coupling shaft extending away from the transducer body; a probe tip coupled with the coupling shaft; a capacitor housed within the transducer body, the capacitor includes: first and second counter electrodes coupled with the transducer body, and a center electrode coupled between the transducer body and the coupling shaft, the center electrode is interposed between the first and second counter electrodes, and the center electrode is movable relative to the first and second counter electrodes; and a shaft support assembly supporting the coupling shaft, the shaft support assembly includes one or more movable support elements, the one or more support elements are coupled between the coupling shaft and the transducer body, and the one or more support elements are spaced from the capacitor along the coupling shaft.

Example 34 can include, or can optionally be combined with the subject matter of one or any combination of Examples 1-33 to optionally include wherein the one or more support elements each include one or more springs.

Example 35 can include, or can optionally be combined with the subject matter of one or any combination of Examples 1-34 to optionally include wherein the one or more support elements are movable to allow one or more of rotation and translation of the center electrode relative to the first and second counter electrodes.

Example 36 can include, or can optionally be combined with the subject matter of one or any combination of Examples 1-35 to optionally include wherein the one or more support elements are deflectable to allow one or more of rotation and translation of the center electrode relative to the first and second counter electrodes.

Example 37 can include, or can optionally be combined with the subject matter of one or any combination of Examples 1-36 to optionally include wherein the one or more support elements of the shaft support assembly include: a proximal support element coupled with the coupling shaft, the proximal support element is proximally spaced from the capacitor, and a distal support element coupled with the coupling shaft, the distal support element is spaced from the capacitor and positioned between the capacitor and the probe tip.

Example 38 can include, or can optionally be combined with the subject matter of one or any combination of Examples 1-37 to optionally include wherein a coupling shaft center of rotation is at the capacitor according to coupling of the proximal and distal support elements with the coupling shaft.

Example 39 can include, or can optionally be combined with the subject matter of one or any combination of Examples 1-38 to optionally include wherein the one or more support elements engage the coupling shaft and transmit static null moments to the coupling shaft, the one or more support elements maintain the probe tip horizontally relative to an unsupported static position.

Example 40 can include, or can optionally be combined with the subject matter of one or any combination of Examples 1-39 to optionally include wherein the one or more support element each include springs, and the springs include a plurality of arms and elbows, and the arms extend arcuately around the coupling shaft.

Example 41 can include, or can optionally be combined with the subject matter of one or any combination of Examples 1-40 to optionally include wherein the one or more support elements continuously extend around the coupling shaft.

Example 42 can include, or can optionally be combined with the subject matter of one or any combination of Examples 1-41 to optionally include wherein the one or more support elements radially engage the coupling shaft around a coupling shaft perimeter, and the one or more support elements laterally support the coupling shaft against lateral movement.

Example 43 can include, or can optionally be combined with the subject matter of one or any combination of Examples 1-42 to optionally include wherein the center electrode is a center electrode assembly including: a center plate, one or more springs extending between the transducer body and the center plate, an upper plate covering the center plate and the one or more springs, the upper plate is coupled with a center plate first face and separated from the transducer body, a lower plate covering the center plate and the one or more springs, the lower plate is coupled with a center plate second face and separated from the transducer body.

Example 44 can include, or can optionally be combined with the subject matter of one or any combination of Examples 1-43 to optionally include wherein the upper plate continuously overlies the entire first counter electrode, and the lower plate continuously overlies the entire second counter electrode.

Example 45 can include, or can optionally be combined with the subject matter of one or any combination of Examples 1-44 to optionally include wherein the upper and lower plates extend from a coupling shaft perimeter to a position immediately adjacent to a transducer body inner perimeter, and the first and second counter electrodes extend from the coupling shaft perimeter to the position immediately adjacent to the transducer body inner perimeter.

Example 46 can include, or can optionally be combined with the subject matter of one or any combination of Examples 1-45 to optionally include wherein the first and second counter electrodes extend to first and second guard rings engaged with the transducer body inner perimeter, and the upper and lower plates extend to a center electrode ring engaged with the transducer body inner perimeter.

Example 47 can include, or can optionally be combined with the subject matter of one or any combination of Examples 1-46 to optionally include wherein one or both of the upper and lower plates include spring recesses sized and shaped to receive the one or more springs during deflection of the one or more springs.

Example 48 can include, or can optionally be combined with the subject matter of one or any combination of Examples 1-47 to optionally include wherein surfaces of the upper and lower plates facing the center plate include the spring recesses, and opposed surfaces of the upper and lower plates are continuously planar.

Example 49 can include, or can optionally be combined with the subject matter of one or any combination of Examples 1-48 to optionally include a method for using a mechanical testing instrument in one or more of nano or micron scale mechanical testing. The method including: engaging a probe tip with a subject, the probe tip is coupled with a coupling shaft and the coupling shaft is coupled with a capacitor, wherein the capacitor includes: a center electrode movable with the coupling shaft, and first and second counter electrodes facing the center electrode assembly, the center electrode is movable relative to the first and second counter electrodes; transmitting at least one excitation signal to the first and second counter electrodes; measuring one or more of displacement of the probe tip and force incident on the probe tip according to measurable electrical characteristics in an output signal received from the center electrode based on the at least one excitation signal; and laterally supporting the coupling shaft with a shaft support assembly, the shaft support assembly includes one or more support elements spaced from the capacitor along the coupling shaft.

Example 50 can include, or can optionally be combined with the subject matter of one or any combination of Examples 1-49 to optionally include wherein measuring one or more of the displacement of the probe tip and force incident on the probe tip includes measuring one or more of displacement of the probe tip and force incident on the probe tip in one or more dimensions including normal and lateral directions.

Example 51 can include, or can optionally be combined with the subject matter of one or any combination of Examples 1-50 to optionally include laterally moving the probe tip across the subject with a piezo actuator coupled with a transducer body housing the capacitor, and the piezo actuator moves the transducer body and the capacitor with the probe tip.

Example 52 can include, or can optionally be combined with the subject matter of one or any combination of Examples 1-51 to optionally include holding the probe tip and the center electrode substantially static relative to the transducer body with the at least one excitation signal transmitted to the first and second counter electrodes, wherein the at least one excitation signal includes static null position voltages.

Example 53 can include, or can optionally be combined with the subject matter of one or any combination of Examples 1-52 to optionally include wherein laterally supporting the coupling shaft with the shaft support assembly including the one or more support elements includes laterally supporting the coupling shaft with one or more deflectable support elements.

Example 54 can include, or can optionally be combined with the subject matter of one or any combination of Examples 1-53 to optionally include moving the center electrode relative to the first and second counter electrodes in one or more dimensions including lateral and normal directions relative to the first and second counter electrodes.

Example 55 can include, or can optionally be combined with the subject matter of one or any combination of Examples 1-54 to optionally include wherein moving the center electrode assembly includes deflecting the one or more support elements.

Example 56 can include, or can optionally be combined with the subject matter of one or any combination of Examples 1-55 to optionally include wherein deflecting the one or more support elements includes deflecting one or more spring elements coupled around the coupling shaft.

Example 57 can include, or can optionally be combined with the subject matter of one or any combination of Examples 1-56 to optionally include wherein deflecting the one or more support elements includes deflecting one or more spring elements coupled continuously around the coupling shaft.

Example 58 can include, or can optionally be combined with the subject matter of one or any combination of Examples 1-57 to optionally include wherein moving the center electrode relative to the first and second counter electrodes includes deflecting one or more springs extending from a center plate of the center electrode, and upper and lower plates of the center electrode cover the one or more springs.

Example 59 can include, or can optionally be combined with the subject matter of one or any combination of Examples 1-58 to optionally include wherein deflecting the one or more springs includes deflecting the one or more springs within recesses between the upper and lower plates.

Example 60 can include, or can optionally be combined with the subject matter of one or any combination of Examples 1-59 to optionally include wherein laterally supporting the coupling shaft with the shaft support assembly includes laterally supporting the coupling shaft with the one or more support elements coupled continuously around the coupling shaft.

Example 61 can include, or can optionally be combined with the subject matter of one or any combination of Examples 1-60 to optionally include wherein laterally supporting the coupling shaft with the shaft support assembly includes laterally supporting the coupling shaft at a proximal position relative to the capacitor with a proximal support element and laterally supporting the coupling shaft at a distal position relative to the capacitor with a distal support element.

Example 62 can include, or can optionally be combined with the subject matter of one or any combination of Examples 1-61 to optionally include wherein laterally supporting the coupling shaft with the shaft support assembly includes constraining the center of rotation of the coupling shaft to a location coincident with the capacitor.

Example 63 combination of Examples 1-62 to optionally include wherein laterally supporting the coupling shaft with the shaft support assembly includes transmitting at least one static null moment to the coupling shaft with the one or more support elements separate from the capacitor.

Example 64 can include, or can optionally be combined with the subject matter of one or any combination of Examples 1-63 to optionally include wherein laterally supporting the coupling shaft includes transmitting respective first and second static null moments to the coupling shaft with proximal and distal support elements of the one or more support elements, the proximal and distal support elements maintaining the probe tip substantially horizontal relative to an unsupported static position.

Example 65 can include, or can optionally be combined with the subject matter of one or any combination of Examples 1-64 to optionally include wherein measuring one or more of the displacement of the probe tip and the force incident on the probe tip includes measuring changes in one or more of capacitance and output voltage of the output signal.

Example 66 can include, or can optionally be combined with the subject matter of one or any combination of Examples 1-65 to optionally include wherein transmitting at least one excitation signal includes transmitting a plurality of excitation signals to respective sections of the first and second electrodes, and measuring one or more of the displacement of the probe tip and the force incident on the probe tip includes measuring electrical characteristics of the output signal including a composite output signal based on the plurality of excitation signals.

Example 67 can include, or can optionally be combined with the subject matter of one or any combination of Examples 1-66 to optionally include wherein receiving the output signal includes receiving the output signal including measurable electrical characteristics corresponding to an overlapping area of the first and second counter electrodes with the upper and lower plates, and the overlapping area extends over one or more springs extending from a center plate of the center electrode.

Example 68 can include, or can optionally be combined with the subject matter of one or any combination of Examples 1-67 to optionally include generating one or more values based on the measured displacement of the probe tip and force incident on the probe tip, the one or more values consisting of at least one of elastic modulus, hardness, coefficient of friction, normal stiffness, and lateral stiffness.

Example 69 can include, or can optionally be combined with the subject matter of one or any combination of Examples 1-68 to optionally include a method for sensing changes in electrical characteristics in a mechanical testing instrument used in one or more of nano or micron scale mechanical testing. The method including: engaging a probe tip with a subject, the probe tip is coupled with a coupling shaft and the coupling shaft is coupled with a capacitor assembly, wherein the capacitor assembly includes: a center electrode assembly movable with the coupling shaft, the center electrode assembly includes upper and lower plates covering a center plate and one or more springs extending from the center plate, and first and second counter electrodes facing the upper and lower plates, each of the first and second counter electrodes includes a plurality of sections, and each of the sections is electrically isolated from the other sections; transmitting a plurality of excitation signals to the plurality of sections, each of the excitation signals associated with each section is different from the excitation signals transmitted to the other sections; and measuring one or more of the displacement of the probe tip and the force incident on the probe tip according to measurable electrical characteristics in a composite output signal received from the center electrode assembly based on the plurality of excitation signals.

Example 70 can include, or can optionally be combined with the subject matter of one or any combination of Examples 1-69 to optionally include wherein measuring one or more of the displacement of the probe tip and force incident on the probe tip includes measuring one or more of displacement of the probe tip and force incident on the probe tip in one or more dimensions including normal and lateral directions.

Example 71 can include, or can optionally be combined with the subject matter of one or any combination of Examples 1-70 to optionally include laterally moving the probe tip across the subject according to the plurality of excitation signals transmitted to the plurality of sections, the plurality of excitation signals moving the center electrode assembly, the coupling shaft and the probe tip.

Example 72 can include, or can optionally be combined with the subject matter of one or any combination of Examples 1-71 to optionally include laterally moving the probe tip across the subject with a piezo actuator coupled with a transducer body housing the capacitor assembly, and the piezo actuator moves the transducer body and the capacitor assembly with the probe tip.

Example 73 can include, or can optionally be combined with the subject matter of one or any combination of Examples 1-72 to optionally include holding the probe tip and the center electrode assembly substantially static relative to the transducer body with the excitation signals applied to the plurality of sections, wherein the excitation signals include static null position voltages.

Example 74 can include, or can optionally be combined with the subject matter of one or any combination of Examples 1-73 to optionally include wherein measuring one or more of the displacement of the probe tip and force incident on the probe tip includes measuring changes in one or more of capacitance and output voltage of each section.

Example 75 can include, or can optionally be combined with the subject matter of one or any combination of Examples 1-74 to optionally include wherein receiving the composite output signal includes receiving the composite output signal including consolidated component output signals, and each of the component output signals has a different specified frequency.

Example 76 can include, or can optionally be combined with the subject matter of one or any combination of Examples 1-75 to optionally include modulating the excitation signals, modulating including: generating the plurality of excitation signals, wherein each excitation signal of the plurality of excitation signals is associated with a different axis of a plurality of axes, and associating each excitation signal of the plurality of excitation signals with a different specified frequency, and each excitation signal includes one of the different specified frequencies.

Example 77 can include, or can optionally be combined with the subject matter of one or any combination of Examples 1-76 to optionally include demodulating the composite output signal, demodulating including: multiplying the composite output signal by one or more of the excitation signals to respectively generate one or more component output signals; and associating each of the one or more component output signals with different axes of the plurality of axes according to the respective excitation signal used in the multiplication.

Example 78 can include, or can optionally be combined with the subject matter of one or any combination of Examples 1-77 to optionally include wherein demodulating includes: filtering each of the one or more component output signals and maintaining a component of each of the one or more component output signals, and wherein the maintained component of each of the one or more component output signals corresponds to one or more of lateral displacement of the probe tip and forces incident on the probe tip along corresponding axes of the plurality of axes.

Example 79 can include, or can optionally be combined with the subject matter of one or any combination of Examples 1-78 to optionally include wherein filtering each of the one or more component output signals includes removing an AC component from the component output signal and maintaining the component includes maintaining a DC component of each of the one or more component output signals, and wherein the DC component of each of the one or more component output signals corresponds to one or more of lateral displacement of the probe tip and forces incident on the probe tip along corresponding axes of the plurality of axes.

Example 80 can include, or can optionally be combined with the subject matter of one or any combination of Examples 1-79 to optionally include supporting the coupling shaft proximally and distally relative to the capacitor assembly.

Example 81 can include, or can optionally be combined with the subject matter of one or any combination of Examples 1-80 to optionally include wherein supporting the coupling shaft proximally and distally includes transmitting static null moments to the coupling shaft from proximal and distal support springs, the proximal and distal support springs maintaining the probe tip substantially horizontal relative to an unsupported static position.

Example 82 can include, or can optionally be combined with the subject matter of one or any combination of Examples 1-81 to optionally include wherein receiving the composite output signal includes receiving the composite output signal including measurable electrical characteristics corresponding to an overlapping area of the first and second counter electrodes with the upper and lower plates, and the upper and lower plates cover the one or more springs.

Example 83 can include, or can optionally be combined with the subject matter of one or any combination of Examples 1-82 to optionally include moving the center electrode assembly relative to the first and second counter electrodes in one or more dimensions including lateral and normal directions relative to the first and second counter electrodes.

Example 84 can include, or can optionally be combined with the subject matter of one or any combination of Examples 1-83 to optionally include deflecting the one or more springs extending from the center plate.

Example 85 can include, or can optionally be combined with the subject matter of one or any combination of Examples 1-84 to optionally include wherein deflecting the one or more springs includes deflecting the one or more springs within spring recesses in one or more of the first and second counter electrodes.

Example 86 can include, or can optionally be combined with the subject matter of one or any combination of Examples 1-85 to optionally include wherein deflecting the one or more springs includes maintaining separation between the one or more springs and the upper and lower plates.

Example 87 can include, or can optionally be combined with the subject matter of one or any combination of Examples 1-86 to optionally include generating one or more values based on the measured displacement of the probe tip and the force incident on the probe tip, the one or more values consisting of at least one of elastic modulus, hardness, coefficient of friction, normal stiffness, and lateral stiffness.

Each of these non-limiting examples can stand on its own, or can be combined in any permutation or combination with any one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A testing instrument for mechanical testing at a one or more of nano or micron scale comprising:
    a transducer body;
    a coupling shaft;
    a probe tip coupled with the coupling shaft; and
    a capacitor housed within the transducer body, the capacitor includes:
        first and second counter electrodes coupled with the transducer body, and
        a center electrode assembly interposed between the first and second counter electrodes, the center electrode assembly is movable with the coupling shaft relative to the transducer body, and the center electrode assembly includes:
            a center plate coupled with the coupling shaft,
            one or more springs coupled between the transducer body and the center plate, the one or more springs extending from the center plate,
            an upper plate covering the center plate and the one or more springs, the upper plate is engaged with a center plate first face, and
            a lower plate covering the center plate and the one or more springs, the lower plate is engaged with a center plate second face, and the center plate and the one or more springs suspend the upper and lower plates.

2. The testing instrument recited in claim 1, wherein the upper plate continuously overlies the entire first counter electrode, and the lower plate continuously overlies the entire second counter electrode.

3. The testing instrument recited in claim 2, wherein the first and second counter electrodes each include two or more electrically isolated sections, and the upper plate continuously overlies each of the two or more sections of the first counter electrode, and the lower plate continuously overlies each of the two or more sections of the second counter electrode.

4. The testing instrument recited in claim 1, wherein the upper and lower plates extend from a coupling shaft perimeter to a position immediately adjacent to a transducer body inner perimeter, and the first and second counter electrodes extend from the coupling shaft perimeter to the position immediately adjacent to the transducer body inner perimeter.

5. The testing instrument recited in claim 1, wherein one or both of the upper and lower plates include spring recesses sized and shaped to receive the one or more springs during deflection of the one or more springs.

6. The testing instrument recited in claim 5, wherein surfaces of the upper and lower plates facing the center plate include the spring recesses, and opposed surfaces of the upper and lower plates facing the first and second counter electrodes are continuously planar.

7. The testing instrument recited in claim 1, wherein the one or more springs extend from a transducer body inner perimeter inwardly to the center plate.

8. The testing instrument recited in claim 7, wherein the center plate extends radially from the coupling shaft to a center plate perimeter adjacent to the transducer body inner perimeter, and the one or more springs extend through the center plate perimeter.

9. The testing instrument recited in claim 1 comprising a shaft support assembly supporting the coupling shaft, the shaft support assembly includes:
    a deflectable proximal support element coupled between the coupling shaft and the transducer body, the proximal support element is proximally spaced from the capacitor,
    a deflectable distal support element coupled between the coupling shaft and the transducer body, the distal support element is distally spaced from the capacitor and positioned between the capacitor and the probe tip,
    wherein one or more of the proximal and distal support elements each include one or more spring elements coupled between the coupling shaft and the transducer body.

10. The testing instrument recited in claim 9, wherein the proximal and distal support elements radially engage the coupling shaft around a coupling shaft perimeter, and the proximal and distal support elements laterally support the coupling shaft against lateral movement of the coupling shaft.

11. A method for using a testing instrument configured for movement or measurement at one or more of a nano or micron scale comprising:
    engaging a probe tip of a coupling shaft with a subject, the coupling shaft is coupled with a capacitor assembly, wherein the capacitor assembly includes:
        a center electrode assembly movable with the coupling shaft, the center electrode assembly includes upper and lower plates engaged to a center plate, the upper and lower plates cover the center plate and one or more springs extending between a transducer body and the center plate, and the center plate and the one or more springs suspend the upper and lower plates, and first and second counter electrodes facing the upper and lower plates;

transmitting at least one excitation signal to the first and second counter electrodes; and measuring one or more of displacement of the probe tip and force incident on the probe tip according to measurable electrical characteristics in an output signal received from the center electrode assembly based on the at least one excitation signal.

12. The method recited in claim 11, wherein measuring one or more of the displacement of the probe tip and force incident on the probe tip includes measuring displacement and force in one or more dimensions including normal and lateral directions.

13. The method recited in claim 11, wherein transmitting at least one excitation signal includes transmitting a plurality of excitation signals to respective sections of the first and second electrodes, and measuring one or more of the displacement of the probe tip and the force incident on the probe tip includes measuring electrical characteristics of the output signal including a composite output signal based on the plurality excitation signals.

14. The method recited in claim 11, wherein receiving the output signal includes receiving the output signal including measurable electrical characteristics corresponding to an overlapping area of the first and second counter electrodes with the upper and lower plates, and the overlapping area extends over the one or more springs.

15. The method recited in claim 11 comprising moving the center electrode assembly relative to the first and second counter electrodes in one or more dimensions including lateral and normal directions relative to the first and second counter electrodes.

16. The method recited in claim 15, wherein moving the center electrode assembly includes deflecting the one or more springs extending between the transducer body and the center plate.

17. The method recited in claim 16, wherein deflecting the one or more springs includes deflecting the one or more springs within spring recesses in one or more of the upper and lower plates.

18. The method recited in claim 17, wherein deflecting the one or more springs includes maintaining separation between the one or more springs and the upper and lower plates.

19. The method recited in claim 11 comprising supporting the coupling shaft proximally and distally relative to the capacitor assembly.

20. The method recited in claim 19, wherein supporting the coupling shaft proximally and distally includes transmitting static null moments to the coupling shaft from proximal and distal support springs, the proximal and distal support springs maintaining the probe tip substantially horizontal relative to an unsupported static position.

* * * * *